Figure 1A:
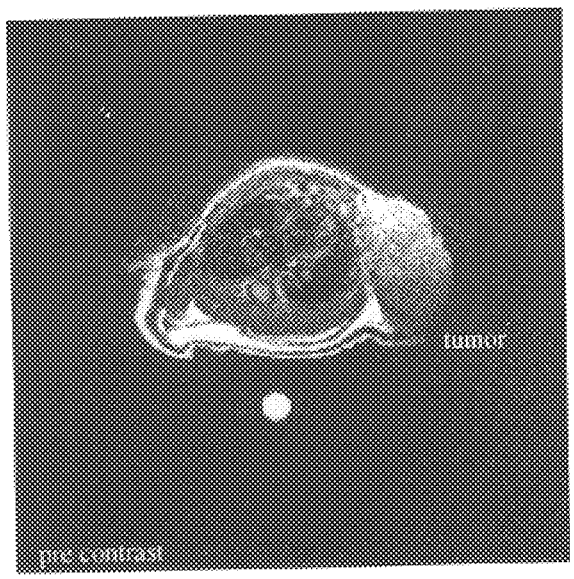
Figure 1B:
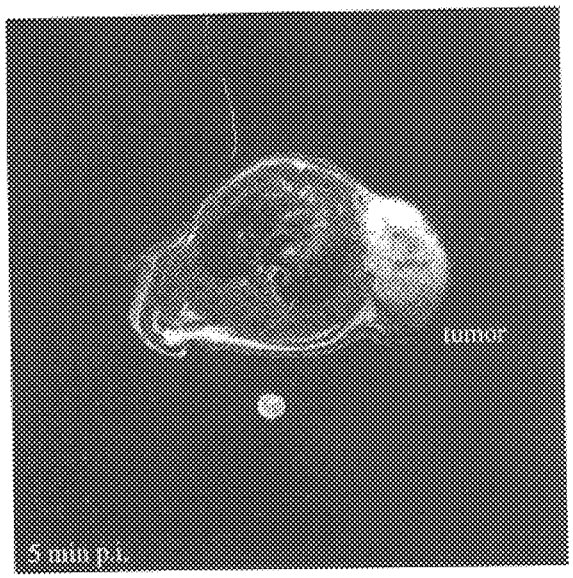
Figure 1C:
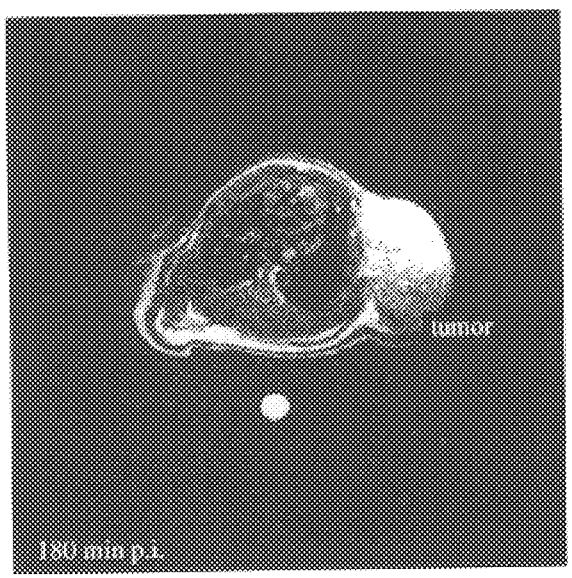
Figure 1D:
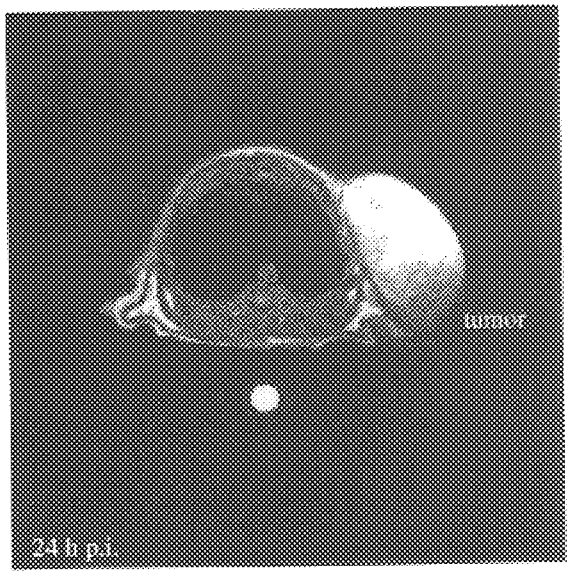
Figure 2A:
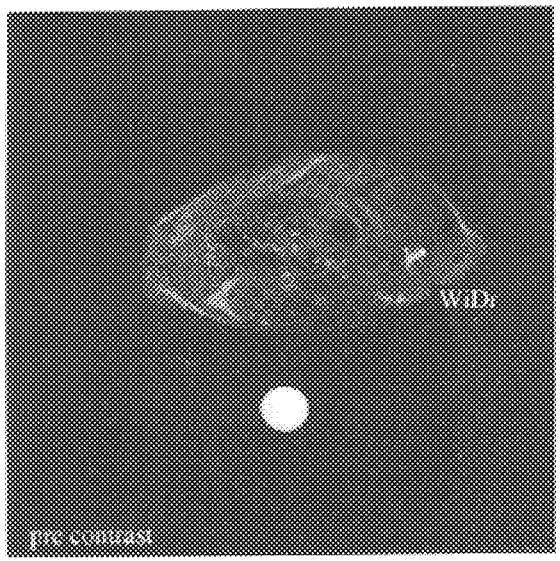
Figure 2B:
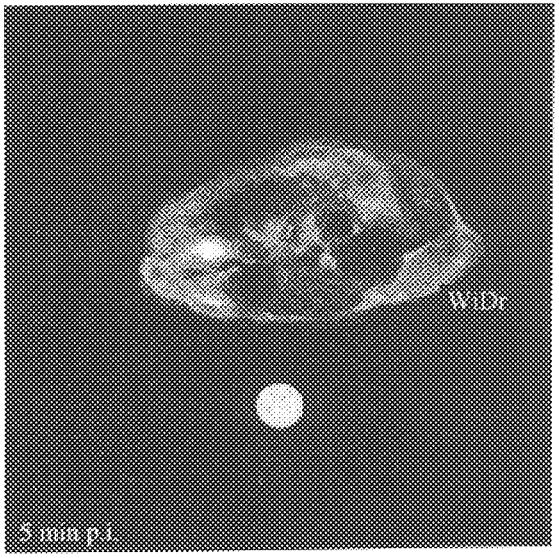
Figure 2C:
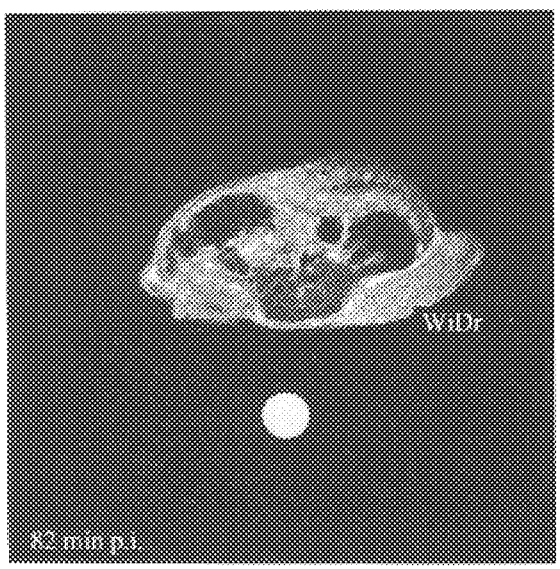
Figure 2D:
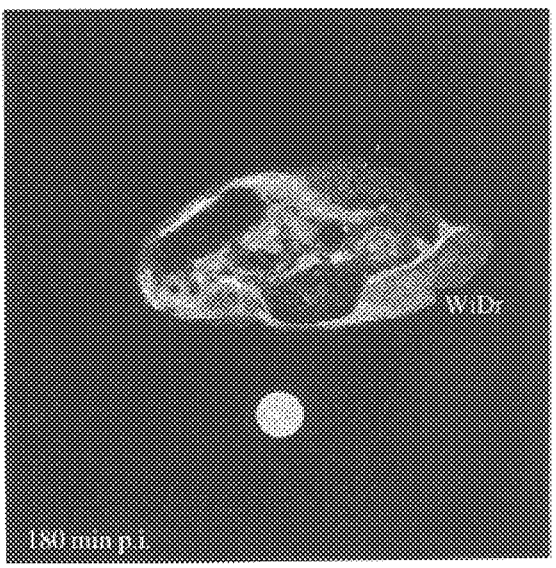
Figure 3A:
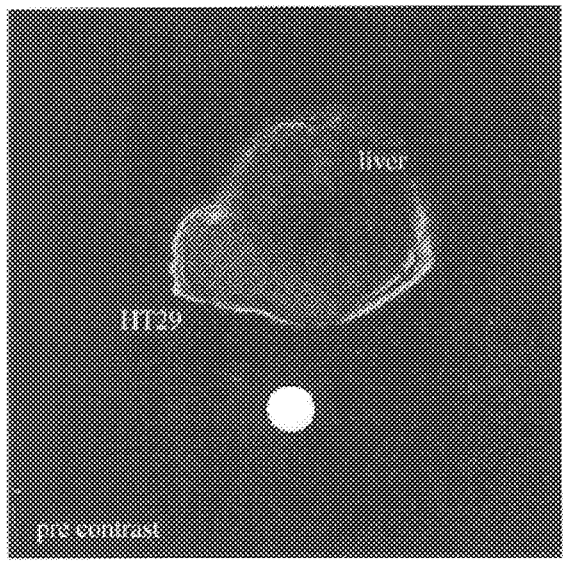
Figure 3B:
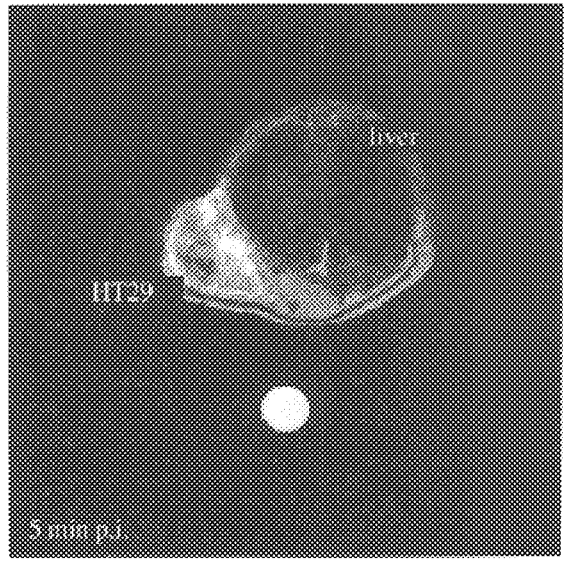
Figure 3C:
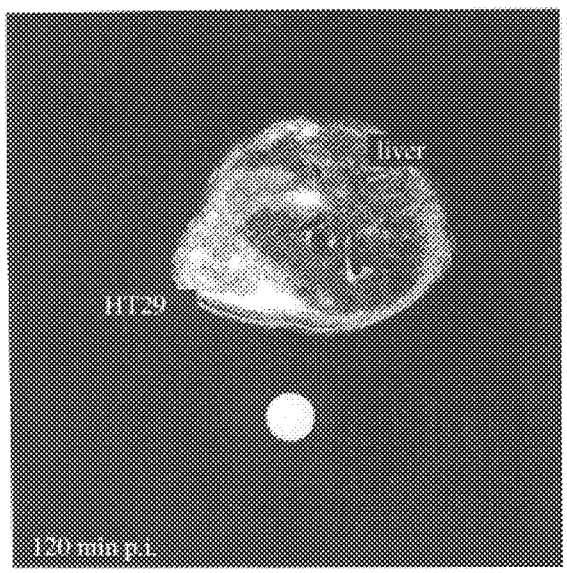
Figure 3D:
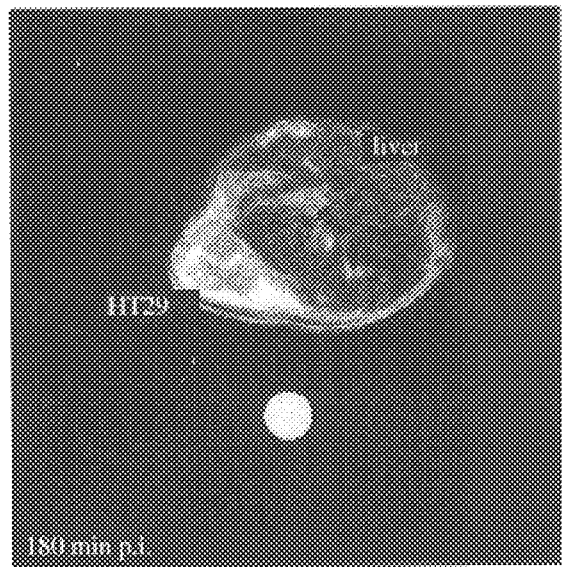

United States Patent [19]
Hilger et al.

[11] Patent Number: 5,849,259
[45] Date of Patent: Dec. 15, 1998

[54] 3-,8-SUBSTITUTED DEUTEROPORPHYRIN DERIVATIVES, PHARMACEUTICAL AGENTS CONTAINING THE LATTER AND PROCESS FOR THEIR PRODUCTION

[75] Inventors: Christoph Stephan Hilger; Franz Karl Maier; Heinz Gries; Ulrich Niedballa; Johannes Platzek; Mary Lee-Vaupel; Wolfgang Ebert; Jürgen Conrad; Josef Gaida, all of Berlin, Germany

[73] Assignee: Institut Fur Diagnostikforschung GmbH, Berlin, Germany

[21] Appl. No.: 406,881

[22] PCT Filed: Sep. 28, 1993

[86] PCT No.: PCT/EP93/02645

§ 371 Date: May 24, 1995

§ 102(e) Date: May 24, 1995

[87] PCT Pub. No.: WO94/07894

PCT Pub. Date: Apr. 14, 1994

[30] Foreign Application Priority Data

Sep. 28, 1992 [DE] Germany .................. 42 32 925.6

[51] Int. Cl.$^6$ .................. A61K 51/00; A61M 36/14
[52] U.S. Cl. .................. 424/1.65; 424/1.11; 424/9.1; 424/9.3; 424/9.4; 424/9.362
[58] Field of Search .................. 424/1.65, 1.11, 424/9.1, 9.3, 9.36, 9.4, 9.42, 9.362; 534/14, 15, 7, 10–16

[56] References Cited

U.S. PATENT DOCUMENTS

| | | | |
|---|---|---|---|
| 4,485,086 | 11/1984 | Wong | 424/1.65 |
| 4,935,498 | 6/1990 | Sessler et al. | 534/15 |
| 5,275,801 | 1/1994 | Niedballa et al. | 424/1.65 |
| 5,283,255 | 2/1994 | Levy et al. | 514/410 |
| 5,371,199 | 12/1994 | Theiren et al. | 534/11 |

*Primary Examiner*—John Kight
*Assistant Examiner*—Dameron Jones
*Attorney, Agent, or Firm*—Millen, White, Zelano, & Branigan, P.C.

[57] ABSTRACT

The invention relates to new 3,8-substituted deuteroporphyrin derivatives with various substituents in positions 13 and 17 of the porphyrin skeleton, pharmaceutical agents containing these compounds, their use in diagnosis and therapy as well as process for the production of these agents.

14 Claims, 4 Drawing Sheets

– ,8-SUBSTITUTED DEUTEROPORPHYRIN DERIVATIVES, PHARMACEUTICAL AGENTS CONTAINING THE LATTER AND PROCESS FOR THEIR PRODUCTION

The invention relates to porphyrin complex compounds with various substituents in positions 3, 8, 13 and 17 of the porphyrin skeleton, pharmaceutical agents containing these compounds, their use in diagnosis as well as process for the production of these compounds and agents.

The use of complexing agents or complexes or their salts in medicine has long been known. As examples can be mentioned: complexing agents as stabilizers of pharmaceutical preparations, complexes and their salts as auxiliary agents for administration of poorly soluble ions (e.g., iron), complexing agents and complexes (preferably calcium or zinc), optionally as salts with inorganic and/or organic bases, as antidotes for detoxification in accidental incorporation of heavy metals or their radioactive isotopes and complexing agents as auxiliary agents in nuclear medicine by using radioactive isotopes such as $^{99m}$Tc for scintigraphy.

Complexes and complex salts have been presented as diagnostic agents, mainly as NMR diagnostic agents, in patents EP 0 071 564, EP 0 139 934 and DE 34 01 052. However, they do not yet optimally meet all requirements which determine the relative effectiveness of an NMR contrast medium, of which the following are to be mentioned as examples:

a favorable relaxivity, so that the contrast medium in the smallest possible concentrations reduces in vivo the relaxation times of the protons in tissue fluids and other nuclei relevant for the NMR (such as phosphorus, fluorine, sodium) and makes possible, for example, the localization of tumors by increasing the signal intensity of the image obtained with the help of the nuclear spin tomograph; a concentration and/or retention of the contrast medium in the target organ as selective as possible; sufficient water solubility; high effectiveness; good compatibility; good chemical and biochemical stability.

Thus above all the two first mentioned points are relevant for imaging. Since the relaxation times between the tissues differ mostly only by the factor of 2–3 (T. E. Budinger and P. C. Lauterbur, Science 226, pp. 288–298, 1984; J. M. S. Hutchinson and F. W. Smith in Nuclear Magnetic Resonance Imaging Edit. C. L. Partain et al., pp. 231–249, Saunders, N.Y. 1983) and the complexes and complex salts of the mentioned patents generally have the drawback that they only spread relatively nonspecifically in the extracellular space and therefore a detection of pathologically changed tissues is not always possible, above all there is a need for selectively binding, tumor-specific compounds that can be used in diagnosis and radiation therapy.

It has been known for some years that porphyrin derivatives selectively accumulate in human and animal tumors (D. Kessel and T.-H. Chou, Cancer Res. 43, pp. 1994–1999, 1983, P. Hambright, Bioinorg. Chem. 5, pp. 87–92, 1975; R. Lipson et al., Cancer 20, pp. 2250–2257, 1967; D. Sanderson et al., Cancer 30, pp. 1368–1372, 1972). First attempts to use this class of compound as diagnostic agents were also described (J. Winkelmann et al., Cancer Research 27, pp. 2060–2064, 1967; N. J. Patronas et al., Cancer Treatment Reports 70, pp. 391–395, 1986).

However, the compounds so far described are far from being able to meet satisfactorily the above-mentioned criteria; their deficient concentration in the target organs still requires special attention. An improvement of this property should at the same time help reduce the existing problems with toxicity and compatibility of the previously known compounds.

Substituted hematoporphyrin complex compounds used in diagnosis and treatment are described in patent application EP 0 355 041.

While these compounds show a good concentration behavior in various target organs, the described compounds used as NMR diagnostic agents have a not yet completely satisfactory ratio between the dose necessary for optimal imaging and the lethal dose. Hematoporphyrin derivatives also have the drawback that they can eliminate both pseudobenzylic OH groups in the hydroxyethyl side chains.

In patent EP 0 071 569 NMR diagnostic agents are described based on DTPA complexes which, while having a favorable safety margin, are excreted relatively quickly as a result of which the examination time remaining with optimal enhancement is only brief.

Derivatives of the deuteroporphyrin have been proposed for tumor imaging with radioisotopes, containing as additional complexing groups polyaminopolycarboxylic acids bound to the porphyrin skeleton by ethylene glycol bridges (Photochemistry and Photobiology Vol. 46, pp. 783–788 (1987)). However, such porphyrin esters are not very suitable for parenteral use in patients—especially for NMR diagnosis—since the injection solutions obtained from them can neither be heat-sterilized nor stored for a sufficiently long time.

Therefore, there remains a demand for many purposes for complex compounds having stable, easily soluble, but also more compatible, more selectively binding over a greater chemical variation range of substituents (which, e.g., make possible the incorporation of metals other than manganese or several, also different, metals and thus at the same time also leads to a control of the properties and uses of the compounds), which, e.g., are suitable for diagnosis and treatment of tumors.

SUMMARY OF THE INVENTION

The object of the invention is thus based on making available such compounds and pharmaceutical agents containing these compounds as well as providing processes for their production.

This object is achieved by the invention.

It was found that porphyrin complex compounds, consisting of a porphyrin ligand, at least one ion of an element with atomic numbers 21–32, 37–39, 42–51 or 57–83 as well as, optionally, cations of inorganic and/or organic bases, surprisingly are excellently suited for the production of NMR and radiodiagnostic agents as well as radiotherapeutic agents.

The porphyrin complex compounds according to the invention of general formula I

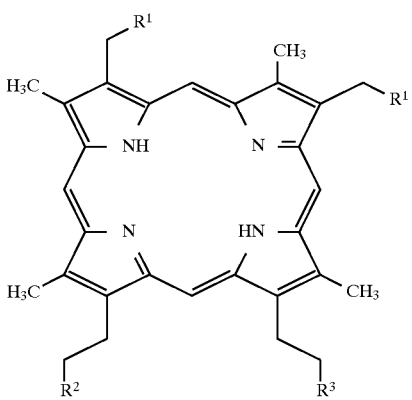

as well as at least one ion of an element with atomic numbers 21–32, 37–39, 42–51 or 57–83, in which $R^1$ stands for a hydrogen atom, for a straight-chain $C_1$–$C_6$ alkyl radical, a $C_7$–$C_{12}$ aralkyl radical or for a group OR' in which R' is a hydrogen atom or a $C_1$–$C_3$ alkyl radical, $R^2$ stands for $R^3$, a group —CO—Z or a group —(NH)$_o$—(A)$_q$—NH—D, in which Z is a group —OL, with L meaning an inorganic or organic cation or is a $C_1$–$C_4$ alkyl radical, A means a phenylenoxy or a $C_1$–$C_{12}$ alkylene or $C_7$–$C_{12}$ aralkylene group interrupted by one or more oxygen atoms, o and q, independently of one another, mean the numbers 0 or 1 and D means a hydrogen atom or a group —CO—A—(COOL)$_o$—(H)$_m$', with m equal to 0 or 1 and provided that the sum of m and o equals 1, $R^3$ stands for a group —(C=M)(NR$^4$)$_o$—(A)$_q$—(NR$^5$)—K, in which M stands for an oxygen atom or for two hydrogen atoms, $R^4$ means a group —(A)$_q$—H and K means a complexing agent of general formula (IIa) or (IIb) and in which $R^5$, if K is a complexing agent of formula (IIa), has the same meaning as $R^4$, and $R^5$, or if K is a complexing agent of formula (IIb), has the same meaning as D, provided that a direct oxygen-nitrogen bond is not allowed, and K stands for a complexing agent of general formula (IIa) or (IIb)

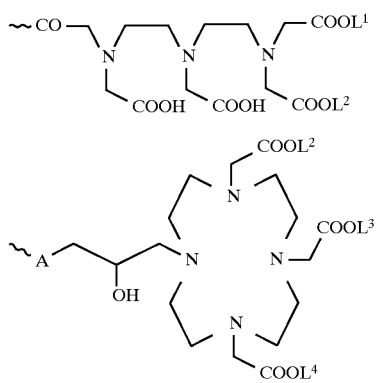

with $L^1$ meaning a $C_1$–$C_6$ alkyl radical or an inorganic or organic cation and in which $L^2$, $L^3$ and $L^4$, independently of one another, have the meaning of $L^1$ or a hydrogen atom, provided that at least two free carboxylic acid groups are present in the complexing agent, as well as optionally other anions to compensate for the charges in the metalloporphyrin.

The complex compounds according to the invention comprise a total of three groups of compounds.

a) Compounds containing a metal ion in the porphyrin, b) compounds containing at least one metal ion in complexing agent radical K and c) compounds containing bound metal ions in both the porphyrin and in complexing agent radical K, in which the metal ions can be different.

Paramagnetic metal ions must be present in the complex to use the agents according to the invention in NMR diagnosis. The latter are especially divalent and trivalent ions of the elements with atomic numbers 21–29, 42, 44 and 57–70. Suitable ions are, for example, chromium(III), manganese(II), manganese(III), iron(III), cobalt(II), cobalt (III), nickel(II), copper(II), praseodymium(II), neodymium (III), samarium(III) and ytterbium(III) ions. Because of their high magnetic moment gadolinium(III), terbium(III), dysprosium(III), holmium(III), erbium(III) and iron(III) ions are especially preferred.

For radiodiagnosis and radiotherapy, complexes are suitable which contain as central atom a radioisotope of elements 27, 29–32, 37–39, 42–51, 62, 64, 70, 75, 77, 82 or 83.

If the concentration, e.g., of an yttrium-90 labeled complex, is to be NMR-diagnostically monitored in use in radiotherapy, complexes are suitable which contain, in addition to the radioisotope, a paramagnetic metal ion as well as another metal ion, preferably a gadolinium ion.

It is possible in this way to combine diagnosis and treatment with the help of the complex conjugates according to the invention.

An essential advantage of the metal complexes containing complexing agent radical K according to the invention is that in the metal complexes, the diagnostic effect brought about by the metal ions can be enhanced by the incorporation of other metal ions.

Surprisingly, the complexes according to the invention in comparison with the structurally similar compounds known so far show a markedly higher relaxivity. Since the relaxivity can be considered as a measure for the contrast medium effectiveness of a compound, in using the complexes according to the invention in the area of NMR diagnosis a comparable, positive signal influencing is possible even with a small dose. In this way, the safety margin increases significantly, for which the product of relaxivity and compatibility can be considered as recommended value.

The complex compounds according to the invention also meet the other requirements, such as, e.g., high selectivity and concentration, in an outstanding way. With the help of the complex compounds according to the invention, surprisingly not only tumor tissues and individual organs can be represented in vivo such as, for example, liver and kidneys, but also blood vessels without using special pulse sequences with which they can be used, i.a., as perfusion agents.

The metals manganese, iron, cobalt, nickel, copper, zinc and technetium can be mentioned as examples for the ions bound in the porphyrin skeleton. Preferred are the metals iron, technetium, zinc and especially manganese.

If one of the ions bound in the porphyrin is present in a higher oxidation stage than +2, then the excess charge(s) is/are balanced, e.g., by anions of organic or inorganic acids, preferably by acetate, chloride, oxide or nitride ions.

The transition metals with atomic numbers 21–30, 37, 39 and 43 as well as the elements 57–83 can be mentioned as examples of the ions bound to complexing agent K. Preferred is the gadolinium, dysprosium, holmium, erbium and manganese ion.

Optionally the carboxyl groups not necessary for the complexing of the metal ions can be present as esters, amides or salts of inorganic or organic bases. Suitable ester radicals are those with 1 to 6 C atoms, preferably the ethyl esters; suitable inorganic cations are, for example, the lithium and potassium ion and, particularly, the sodium ion. Suitable cations of organic bases are those of primary, secondary or tertiary amines, such as, for example, ethanolamine, diethanolamine, morpholine, glucamine, N,N-dimethylglucamine, especially meglumine.

As examples for the group —$(NR^4)_o$—$(A)_q$—$(NR^5)$— which, in a way, serves as "linker" between the porphyrin skeleton and complexing agent K, there can be mentioned, for example, the —NHNH—, —NH(CH$_2$)$_2$NH—, —NH(CH$_2$)$_3$NH—, —NH(CH$_2$)$_4$NH—, —NH(CH$_2$)$_2$O(CH$_2$)$_2$NH—, —NH—CH$_2$—C$_6$H$_4$—CH$_2$—NH— and the —CH$_2$—O—C$_6$H$_4$NH—group.

As complexing agent radicals K, preferably derivatives of diethylenetriaminepentaacetic acid and the 1,4,7,10-tetraazacyclododecane-1,4,7-triacetic acid can be mentioned, which are bound by a "linker" to the respective porphyrin.

The production of the complex compounds according to the invention takes place in that by a) reduction of a porphyrin of general formula (IIIa)

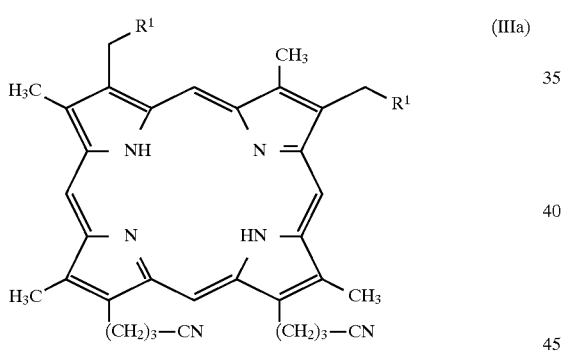

or by b) reaction of a porphyrin of general formula (IIIb)

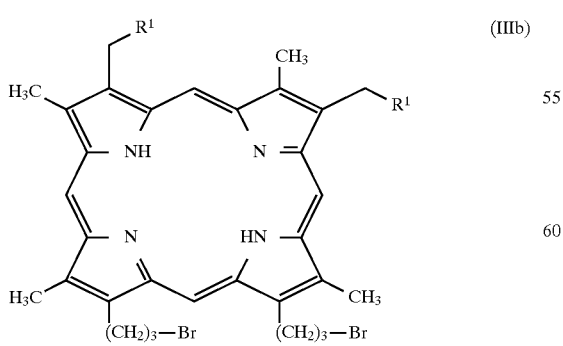

with aminophenol, or by c) reaction of a porphyrin of general formula (IIIc)

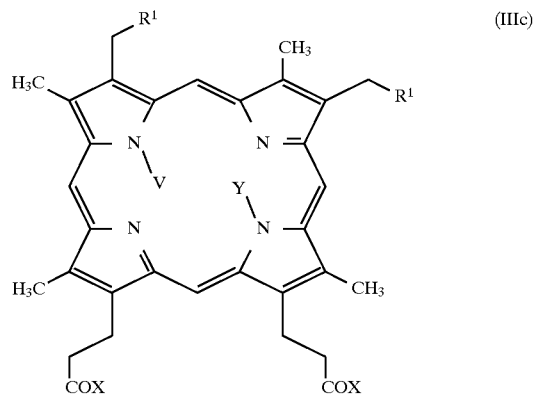

in which $R^1$ has the indicated meaning,

V and Y each stand for a hydrogen atom or together for a multivalent metal ion of an element with atomic numbers 21–32, 37–39, 42–51 or 57–83, preferably for a zinc(II) or a manganese(III) ion and X stands for a halogen atom, a group —OR' or for a group —O—COOR' with R' in the mentioned meaning, with compounds H—$NR^4$—$(A)_q$—$NR^4$—H, in which A, $R^4$ and q have the indicated meaning, optionally subsequent reduction of the carbonyl groups or Hofmann degradation of the amide first yields a porphyrin of general formula IV

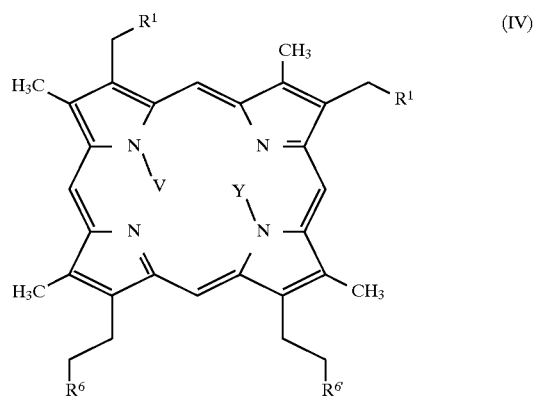

in which $R^6$ stands for a group —(C=M)—$(NR^4)_o$—$(A)_q$—$NR^4$—H, in which M, $R^4$, A, o and q have the indicated meaning and in which $R^{6'}$ has the same meaning as $R^6$ or stands for a group —OR', that then a) is reacted with a complexing agent of general formula V,

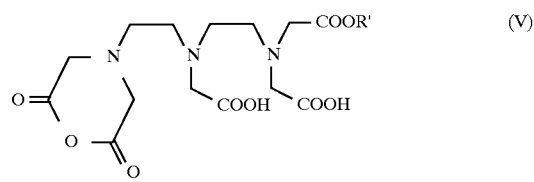

in which R' has the indicated meaning, and optionally the present ester groups are saponified or b) is reacted with a compound of formula VI

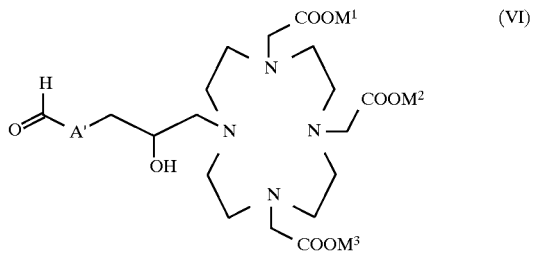

in which A' is a group A shortened by a carbon atom and $M^1$, $M^2$ and $M^3$, independently of one another, stand for R' or a metal ion equivalent of the elements with atomic numbers 21–32, 37–39, 42–51 or 57–83, under the conditions of a reductive amination, then the thus obtained product—optionally after complete or partial cleavage of the ester groups—is reacted with (a) metal oxide(s) or metal salt(s) of the elements of the above-mentioned atomic numbers, then acylated with a nucleofuge-D' reagent (and the last-mentioned steps can be interchanged) in which D' has the meaning indicated under D, with the provision that D' does not stand for hydrogen and then, optionally, acidic hydrogens optionally possibly still present are then completely or partially substituted by cations of inorganic or organic bases.

As examples, acetyl chloride, acetic anhydride, succinic acid anhydride or diglycolic acid anhydride can be mentioned as nucelofuge-D'.

Thus, the functionalization of the C-13 and C-17 side-chains to C-13,17-amino- or amidoalkyl-substituted porphyrin derivatives (serving as feedstocks for the porphyrin complexes according to the invention containing complexing agent K) takes place either by a) reduction of the respective 13,17-bis-(3-cyanopropyl)-porphyrin to the amine in a way known in the art, for example, with lithium borohydride/trimethylsilyl chloride in an organic polar ether, preferably tetrahydrofuran (A. Giannis, K. Sandhoff, Angew. Chem.; 101 (1989) 220/22) or b) reaction of the respective 13,17-bis-(3-bromopropyl)-porphyrin with an aminophenol in a dipolar aprotic solvent such as, e.g., dimethylformamide or dimethyl sulfoxide or c) reaction of the desired C-13,17-propionic acid chain-carrying porphyrins which optionally can be present in active form, e.g., as acid chlorides, esters or mixed anhydrides, optionally containing a metal atom instead of the pyrrolic hydrogens, with optionally substituted hydrazines or with terminal alkylenediamines which optionally can be substituted by a $C_1$–$C_6$ alkyl, aryl or $C_7$–$C_{12}$ aralkyl radical and from which an amino group optionally, e.g., in the form of a carbobenzoxy or t-butoxycarbonyl radical, is protected. The removal of the protective groups then takes place according to methods known in the literature, e.g., by hydrogenation or treatment with trifluoroacetic acid or with hydrochloric acid/glacial acetic acid.

If asymmetrically substituted porphyrins are to be produced, i.e., porphyrins in which the radicals $R^2$ and $R^3$ are not the same, then this can be controlled by the reaction time and stoichiometry.

The introduction of complexing agent radical K of general formula IIa in the thus functionalized C-13, C-17 amino- or amidoalkyl-substituted porphyrin derivatives takes place in a way known in the art by reaction with the corresponding acid anhydrides in liquid phase. Suitable reagents are, for example, water, dipolar aprotic solvents, such as dimethylformamide, dimethyl sulfoxide or hexamethylphosphoric acid triamide in the presence of an inorganic or organic base, such as alkali or alkaline-earth hydroxides and carbonates and tertiary amines such as, e.g., trimethylamine, triethylamine, N,N'-dimethylaminopyridine. Suitable reaction temperatures are between −10° and 120° C., preferably between 0° and 50° C.

The introduction of radical K of general formula IIb takes place in a way known in the art, by a corresponding initial product, that optionally can already be substituted by a metal, being reacted by glycol cleavage (e.g., with periodate) first to an aldehyde of general formula VI and then being reacted with the respective C-13, C-17 amino- or amidoalkyl-substituted porphyrin derivative. A reduction, e.g., with sodium cyanoborohydride follows this reaction step.

Remaining secondary amines can be acylated by reaction with activated acid derivatives (nucleofuge-D').

The introduction of the desired metals (e.g., Mn, Fe, Co, Ni, Cu, Zn, Tc, Sm, Eu, Gd, Bi) in the porphyrins takes place according to methods known in the literature (The Porphyrins, ed. D. Dolphin, Academic Press, New York 1980, Vol. V, p. 459) and essentially there can be mentioned:

a) the substitution of the pyrrolic NH's (by heating of the metal-free ligands with the corresponding metal salt, preferably the acetate, optionally with addition of acid buffering agents, such as, e.g., sodium acetate, in a polar solvent) or b) the "recomplexing," in which a metal already complexed by the ligand is displaced by the desired metal.

As solvents, primarily polar solvents, such as, e.g., methanol, glacial acetic acid, dimethylformamide, chloroform and water, are suitable.

The introduction of the porphyrin metal can take place before or after joining of complexing agent radical K as well as before or after chelating of this complexing agent with a metal. In this way, an especially flexible process for the synthesis of the compounds according to the invention is made possible so that, e.g., metal isotopes of little half-life (for example 99m-technetium), can be introduced only in the final synthesis step either in the porphyrin ligand or in the complexing agent.

The chelating of radical K takes place in a way known in the literature (see, e.g., DE 34 01 052) by the metal oxide or metal salt (e.g., the nitrate, acetate, carbonate, chloride or sulfate) of the respectively desired metal being suspended or dissolved in polar solvents, such as water or aqueous alcohols, and reacted with the corresponding amount of the complexing ligand. If desired, any present acidic hydrogen atoms or acid groups can be substituted by cations of inorganic and/or organic bases or amino acids.

The neutralization takes place in this case with the help of inorganic bases, such as, e.g., alkali or alkaline-earth hydroxides, carbonates or bicarbonates and/or organic bases such as, i.a., primary, secondary or tertiary amines, such as, e.g., ethanolamine, morpholine, glucamine, N-methyl- and N,N-dimethylglucamine, as well as basic amino acids, such as, e.g., lysine, arginine and ornithine or of amides of initially neutral or acidic amino acids.

For production of the neutral complex compounds, for example, enough of the desired bases can be added to the acid complex salts in aqueous solution or suspension that the neutralization point is reached. The obtained solution can then be evaporated to dryness in a vacuum. Often, it is advantageous to precipitate the formed neutral salts by addition of water-miscible solvents, such as, for example, lower alcohols (e.g., methanol, ethanol, isopropanol), lower ketones (e.g., acetone), polar ethers (e.g., tetrahydrofuran, dioxan, 1,2-dimethoxyethane) and thus to obtain easy-to-isolate and readily-purified crystallizates. It has proven especially advantageous to add the desired base as early as during the complexing of the reaction mixture and therefore to eliminate a process step.

If the acid complex compounds contain several free acidic groups, it is often advisable to produce neutral mixed salts containing both inorganic and organic cations as counterions.

This can happen, for example, by the complexing ligands in an aqueous suspension or solution being reacted with the oxide or salt of the element supplying the central ion and half of the amount of an organic base necessary for the neutralization, the formed complex salt being isolated, optionally purified and then mixed with the necessary amount of inorganic base for complete neutralization. The sequence of the addition of bases can also be reversed.

Another possibility of achieving neutral complex compounds is to convert the remaining acid groups in the complex totally or partially into esters. This can occur by a later reaction on the completed complex (e.g., by exhaustive reaction of the free carboxy groups with dimethyl sulfate).

If complex compounds containing radioisotopes are used, their production can be carried out according to the methods described in "Radiotracers for Medical Applications," Volume 1, CRC-Press, Boca Raton, Fla.

The production of the pharmaceutical agents according to the invention also takes place in a way known in the art, by the complex compounds according to the invention— optionally with addition of additives usual in galenicals— being suspended or dissolved in an aqueous medium and then the suspension or solution optionally being sterilized. Suitable additions are, for example, physiologically harmless buffers (such as, e.g., tromethamine), small additions of complexing agents (such as, e.g., diethylenetriaminepentaacetic acid) or, if necessary, electrolytes such as, e.g., sodium chloride or, if necessary, antioxidants, such as, e.g., ascorbic acid.

If, for enteral administration or other purposes, suspensions or solutions of the agents according to the invention in water or in physiological salt solution are desired, they are mixed with one or more adjuvant(s) usual in galenicals (e.g., methyl cellulose, lactose, mannitol) and/or surfactant(s) (e.g., lecithins, Tween®, Myrj® and/or aromatic substances for taste correction (e.g., essential oils).

In principle, it is also possible to produce the pharmaceutical agents according to the invention without isolation of the complex salts. Special care must always be taken that chelation be carried out so that the salts and salt solutions according to the invention are practically free of noncomplexed toxically-acting metal ions.

This can be assured, for example, with the help of color indicators such as xylenol orange by control titrations during the production process. The invention also relates therefore to processes for the production of the complex compounds and their salts. Purification of the isolated complex salt remains as final safety measure.

To avoid unwanted photoreactions of the porphyrins, the compounds and agents according to the invention should be stored and handled as much as possible with exclusion of light.

The pharmaceutical agents according to the invention contain preferably 20 μmol/L to 200 mmol/L of the complex salt and are generally dosed in amounts of 0.01 μmol to 2 mmol/kg of body weight. They are intended for enteral and parenteral administration.

The complex compounds according to the invention are used 1. in NMR diagnosis in the form of their complexes with the ions of elements with atomic numbers 21–30, 42, 44 and 57–83;
2. in radiodiagnosis and radiotherapy in the form of their complexes with the isotopes of elements with atomic numbers 2, 29–32, 37–39, 42–51, 62, 64, 70, 75, 77, 82 or 83.

The agents according to the invention meet the varied requirements for suitability as contrast media for nuclear spin tomography. Thus, they are outstandingly suitable after enteral or parenteral administration to improve the informative value of the image obtained with the help of the nuclear spin tomograph by increasing the signal intensity. Further, they show the high effectiveness necessary to load the body with the least possible amounts of foreign substances and the good compatibility necessary to maintain the noninvasive nature of the tests.

The good water solubility of the agents according to the invention allows the production of highly concentrated solutions, so that the volume load of the circulatory system is kept within justifiable limits and the dilution by body fluids is offset. Further, the agents according to the invention not only show at high stability in vitro, but also a surprisingly high stability in vivo, so that a release or an exchange of the ions—toxic in themselves—bound noncovalent in the complexes is insignificant within the time in which the new contrast media are completely reexcreted.

Details of the use are discussed, for example, in H. J. Weinmann et al., Am. J. of Roentgenology 142, 619 (1984).

The agents according to the invention, because of their advantageous radioactive properties and the good stability of the complex compounds contained in them, are also suitable as radiodiagnostic agents. Details regarding the use and dosage of the complex compounds according to the invention carrying the radioactive metal ions in the field of radiodiagnosis are described, e.g., in "Radiotracers for Medical Applications," CRS-Press, Boca Raton, Fla.

Another imaging method with radioisotopes is the positron emission tomography, which uses positron-emitting isotopes, such as, e.g., $^{43}$Sc, $^{44}$Sc, $^{52}$Fe, $^{55}$Co and $^{68}$Ga (Heiss, W. D., Phelps, M. E., Positron Emission Tomography of Brain, Springer Verlag Berlin, Heidelberg, N.Y. 1983).

The compounds according to the invention can also be used in radioimmuno or radiation treatment. The latter is differentiated from the corresponding diagnosis only by the type and the amount of the isotope used. The purpose is thus the destruction of tumor cells by high-energy shortwave radiation with a smallest possible range of action. Suitable β-emitting ions are, for example, $^{46}$Sc, $^{47}$Sc, $^{48}$Sc, $^{72}$Ga, $^{73}$Ga and $^{90}$Y. Suitable α-emitting ions having short half-lives are, e.g., $^{211}$Bi, $^{212}$Bi, $^{213}$Bi, $^{214}$Bi and $^{212}$Bi is preferred. A suitable photon- and electron-emitting ion is $^{158}$Gd, which can be obtained from $^{157}$Gd by neutron capture.

If the agent according to the invention is intended for use in the variant of radiation treatment proposed by R. L. Mills et al. [Nature Vol. 336, (1988), p. 787], the complexed ion(s) must be derived from a Mössbauer isotope, such as, for example, $^{57}$Fe or $^{151}$Eu.

In the in vivo administration of the therapeutic agents according to the invention, the agents can be administered together with suitable vehicles, such as, e.g., serum or physiological common salt solution and together with another protein, such as, e.g., human serum albumin. In this case, the dosage is dependent on the type of cellular disorder, the metal ion used and the type of method, e.g., brachytherapy.

The therapeutic agents according to the invention are administered parenterally.

Details of the use of radiotherapeutic agents are discussed, e.g., in R. W. Kozak et al. TIBTEC, October 1986, 262.

The invention is explained by the following examples:

EXAMPLE 1 a) N,N'-Bis[9-carboxy-2,5-bis(carboxymethyl)-8-(ethoxycarboxymethyl-2,5,8-triazanonyl-carbamoyl]-mesoporphyrin-IX-13,17-diamide 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 mmol) of triethylamine and 595 mg (1 mmol) of mesoporphyrin-IX-13,17-dihydrazide (produced analogously to H. Fischer, E. Haarer and F. Stadler, Z. Physiol. Chem. 241, 209 (1936)) are added and the resulting reaction mixture is stirred for 3 days at room temperature. After completion of the reaction, it is filtered, the solvent is removed in a vacuum and the remaining oil triturated with 500 ml of diethyl ether. The precipitated solid is filtered off and washed with diethyl ether and n-hexane. For purification, it is chromatographed on silica gel RP-18 (Eluent: $H_2O$/tetrahydrofuran; tetrahydrofuran: 0–30%).

Yield: 1.21 g (86.3% of theory) of reddish brown powder

Analysis (relative to the anhydrous substance): C 56.56 H 6.62 N 13.99 O 22.83 Cld. C 56.25 H 6.89 N 13.70 b) N,N'-Bis[9-carboxylato-2,5-bis(carboxylatomethyl)-8-(ethoxycarboxymethyl-2,5,8-triazanonyl-carbamoyl]-mesoporphyrin-IX-13,17-diamide, digadolinium complex 1.40 g (1 mmol) of the ligand produced in example 1a is dissolved in 400 ml of water. By addition of 2 n aqueous sodium hydroxide solution, it is adjusted to pH 7 and alternately 894.2 mg (2.2 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, the solvent is removed in a vacuum and the residue is chromatographed on silica gel RP-18 (Eluent: $H_2O$ /tetrahydrofuran; tetrahydrofuran: 0–30%).

Yield: 1.01 g (59.1% of theory) of reddish brown powder

Analysis (relative to the anhydrous substance): C 46.36 H 5.07 N 11.47 Gd 18.39 O 18.71 Cld. C 46.08 H 5.29 N 11.27 Gd 18.05 c) N,N'-Bis[9-carboxylato-2,5,8-tris(carboxylatomethyl)-2,5,8-triazanonyl-carbamoyl]-mesoporphyrin-IX-13,17-diamide, digadolinium complex, disodium salt 1.4 g (1 mmol) of the ligand produced in example 1a is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7.0 with concentrated hydrochloric acid and, as described in example 1b, complexed, worked up and purified with 894.2 mg (2.2 mmol) of gadolinium acetate tetrahydrate.

Yield: 1.19 g (70.1% of theory) of reddish brown powder

Analysis (relative to the anhydrous substance): C 43.88 H 4.51 Gd 18.53 Na 2.71 O 18.85 Cld. C 43.71 H 4.30 Gd 18.28 Na 2.80

EXAMPLE 2 a) N,N'-Bis[13-carboxy-4-oxo-6,9-bis-(carboxymethyl)-12-(ethoxycarboxymethyl)-3,6,9,12-tetraazatridecyl]-mesoporphyrin-IX-13,17-diamide 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 mmol) of triethylamine and 650.9 mg (1 mmol) of N,N'-bis(2-aminoethyl)-mesoporphyrin-IX-diamide (produced analogously to H. Fischer, E. Haarer and F. Stadler, Z. Physiol. Chem. 241, 209 (1936)) are added and the resulting reaction mixture is stirred for 3 days at room temperature. After completion of the reaction, it is filtered, the solvent is removed in a vacuum and the remaining oil is triturated with 500 ml of diethyl ether. The precipitated solid is washed with diethyl ether and hexane. For purification, it is chromatographed on silica gel RP-18 (Eluent: $H_2O$/tetrahydrofuran; tetrahydrofuran: 0–30%).

Yield: 1.21 g (82.3% of theory) of reddish brown powder

Analysis (relative to the anhydrous substance): C 57.68 H 6.92 N 13.45 O 21.95 Cld. C 57.39 H 7.18 N 13.22 b) N,N'-Bis[13-carboxy-4-oxo-6,9-bis-(carboxymethyl)-12-(ethoxycarboxymethyl)-3,6,9,12-tetraazatridecyl]-mesoporphyrin-IX-13,17-diamide, digadolinium complex 1.458 g (1 mmol) of the ligand produced in example 2a is dissolved in 400 ml of water. By addition of 2 n aqueous sodium hydroxide solution, it is adjusted to pH 7 and alternately 894.2 mg (2.2 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 (Eluent: $H_2O$/tetrahydrofuran; tetrahydrofuran: 0–30%).

Yield: 1.33 g (73.3% of theory) of reddish brown powder

Analysis (relative to the anhydrous substance): C 47.61 H 5.37 N 11.10 Gd 17.81 O 18.12 Cld. C 47.32 H 5.52 N 10.85 Gd 17.69 c) N,N'-Bis[13-carboxylato-4-oxo-6,8,12-tris-(carboxylatomethyl)-3,6,9,12-tetraazatridecyl]-mesoporphyrin--IX-3,17-diamide, digadolinium complex, disodium salt 1.458 g (1 mmol) of the ligand produced in example 2a is dissolved in 400 ml of water. By addition of 10 molar aqueous sodium hydroxide solution, it is adjusted to pH 13 and stirred for 5 hours to room temperature. After completion of the saponification of the ester groups, it is adjusted to pH 7 with concentrated hydrochloric acid and, as described in example 2b, complexed, worked up and purified with 894.2 mg (2 mmol) of gadolinium acetate tetrahydrate.

Yield: 980 mg (55.9% of theory) of reddish brown powder

Analysis (relative to the anhydrous substance): C 45.20 H 4.83 N 11.18 Gd 17.93 Na 2.62 O 18.24 Cld. C 44.92 H 5.09 N 10.99 Gd 17.71 Na 2.71

EXAMPLE 3 a) N,N'-Bis-(3-aminopropyl)-mesoporphyrin-IX-13,17-diamide 1 g (1.68 mmol) of mesoporphyrin-IX-dimethyl ester is suspended in a sealing tube in 300 ml of 1,3-diaminopropane and 200 ml of absolute pyridine. After covering with nitrogen, it is heated in the sealing tube for 3 days to 150° C. After completion of the reaction, it is concentrated by evaporation in a vacuum and the residue repeatedly recrystallized from pyridine/diethyl ether.

Yield: 930 mg (81.5% of theory) of reddish brown powder

Analysis (relative to the anhydrous substance): C 70.76 H 8.02 N 16.50 O 4.71 Cld. C 70.49 H 8.12 N 16.31 b) N,N'-Bis[14-carboxy-5-oxo-7,10-bis-(carboxymethyl)-13-(ethoxycarboxymethyl)-4,7,10,13-tetraazatetradecyl]-mesoporphyrin-IX-13,17-diamide 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 mmol) of triethylamine and 679 mg (1 mmol) of N,N'-bis(3-aminopropyl)-mesoporphyrin-IX-13,17-diamide (example 3a) are added and the resulting reaction mixture is stirred for 3 days at room temperature. After completion of the reaction, it is filtered, the solvent is removed in a vacuum and the remaining oil is triturated with 500 ml of diethyl ether. The precipitated solid is washed with diethyl ether and hexane. For purification, it is chromatographed on silica gel RP-18 (Eluent: $H_2O$/tetrahydrofuran; tetrahydrofuran: 0–30%).

Yield: 1.20 g (80.8% of theory) of reddish brown powder
Analysis (relative to the anhydrous substance): C 58.21 H 7.06 N 13.20 O 21.40 Cld. C 57.93 H 7.24 N 13.01 c) N,N'-Bis[14-carboxylato-5-oxo-7,10-bis-(carboxylatomethyl)-13-(ethoxycarboxymethyl)-4,7,10,13-tetraazatetradecyl]-mesoporphyrin-IX-13,17-diamide, digadolinium complex 1.49 g (1 mmol) of the ligand produced in example 3b) is dissolved in 400 ml of water. By addition of 2 n aqueous sodium hydroxide solution, it is adjusted to pH 7 and alternately 89,4.2 mg (2.2 mmol) of gadolinium acetate tetrahydrate and 2 n aqueous sodium hydroxide solution are added in portions, so that the pH of the reaction mixture always fluctuates between 6.8 and 7.2. After all After all gadolinium acetate has been added, it is stirred overnight at room temperature. For working-up, it is filtered, the solvent is removed in a vacuum and the residue is chromatographed on silica gel RP-18 (Eluent: $H_2O$/tetrahydrofuran; tetrahydrofuran: 0–30%).

Yield: 1.01 g (56.3% of theory) of reddish brown powder
Analysis (relative to the anhydrous substance): C 48.20 H 5.51 N 10.93 Gd 17.53 O 17.83 Cld. C 47.95 H 5.71 N 10.71 Gd 17.24 d) N,N'-Bis[14-carboxylato-5-oxo-7,10,13-tris-(carboxylatomethyl) -4,7,10, 13-tetraazatetradecyl]-mesoporphyrin-IX-13,17-diamide, digadolinium complex, disodium salt 1.49 g (1 mmol) of the ligand produced in example 3b) is dissolved in 400 ml of water. By addition of 10 molar aqueous; sodium hydroxide solution, it is adjusted to pH 13 and stirred for 5 hours at room temperature. After completion of the saponification of the ester groups, it is adjusted to pH 7 with concentrated hydrochloric acid and, as described in example 3c, complexed, worked up and purified with 894.2 mg (2.2 mmol) of gadolinium acetate tetrahydrate.

Yield: 935 mg (52.5% of theory) of reddish brown powder
Analysis (relative to the anhydrous substance): C 45.83 H 4.98 N 11.00 Gd 17.65 Na 2.58 O 17.96 Cld. C 45.58 H 5.13 N 10.79 Gd 17.45 Na 2.72

EXAMPLE 4 a) N,N'-Bis(4-aminobutyl)-mesoporphyrin-IX-13,17-diamide 1 g (168 mmol) of mesoporphyrin-IX-dimethyl ester is suspended in a sealing tube in 300 ml of melted 1,4-diaminobutane and 200 ml of absolute pyridine. After covering with nitrogen, it is heated in a sealing tube for 3 days to 150° C. It is concentrated by evaporation in a vacuum, the residue is mixed with 500 ml of diethyl ether, the precipitated solid is filtered off and rewashed with plenty of diethyl ether. The crude product is purified by recrystallization from pyridine/diethyl ether.

Yield: 953 mg (80.21% of theory) of reddish brown powder
Analysis (relative to the anhydrous substance): C 71.35 H 8.27 N 15.85 O 4.53 Cld. C 71.08 H 8.10 N 15.57 b) N,N'-Bis[15-carboxy-6-oxo-8,11-bis-(carboxymethyl)-14-(ethoxycarboxymethyl)-5,8,11,14-tetraazapentadecyl]-mesoporphyrin-IX-13,17-diamide 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 ),mmol) of triethylamine and 707 mg (1 mmol) of N,N'-bis-(4-aminobutyl)-mesoporphyrin-IX-13,17-diamide (example 4a) are added and the resulting reaction mixture is stirred for 3 days at room temperature. After completion of the reaction, it is filtered, the solvent is removed in a vacuum and the remaining oil is triturated with 500 ml of diethyl ether. The precipitated solid is filtered off and washed with diethyl ether and hexane. For purification, it is chromatographed on silica gel RP-18 (Eluent: $H_2O$/tetrahydrofuran; tetrahydrofuran: 0–30%).

Yield: 1.24 g (81.9% of theory) of reddish brown powder
Analysis (relative to the anhydrous substance): C 58.72 H 7.19 N 12.95 O 21.14 Cld. C 58.51 H 7.28 N 12.68 c) N,N'-Bis[15-carboxylato-6-oxo-8,11-bis-(carboxylatomethyl)-14-(ethoxycarboxymethyl)-5,8,11,14-tetraazapentadecyl]-mesoporphyrin-IX-13,17-diamide, digadolinium complex 1.51 g (1 mmol) of the ligand produced in example 4b is dissolved in 400 ml of water. By addition of 2 n aqueous sodium hydroxide solution, it is adjusted to pH 7 and alternately 894.2 mg (2.2 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 (Eluent: $H_2O$/tetrahydrofuran; tetrahydrofuran: 0–30%).

Yield: 1.31 g (71.9% of theory) of reddish brown powder
Analysis (relative to the anhydrous substance): C 48.78 H 5.64 N 10.76 Gd 17.26 O 17.56 Cld. C 48.49 H 5.83 N 10.48 Gd 17.06 d) N,N'-Bis[15-carboxylato-6-oxo-8,11,14-tris-(carboxylatomethyl)-5,8,11,14-tetraazapentadecyl]-mesoporphyrin-IX-13,17-diamide, digadolinium complex, disodium salt 1.51 g (1 mmol) of the ligand produced in example 4b is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7 with concentrated hydrochloric acid and, as described in example 4c, complexed, worked up and purified with 894.2 mg (2.2 mmol) of gadolinium acetate tetrahydrate.

Yield: 1.29 g (71.3% of theory) of reddish brown powder
Analysis (relative to the anhydrous substance): C 46.45 H 5.12 N 10.83 Gd 17.37 Na 2.54 O 17.68 Cld. C 46.42 H 5.23 N 10.75 Gd 17.27 Na 2.61

EXAMPLE 5 a) N,N'-Bis(5-aminopentyl)-mesoporphyrin-IX-13,17-diamide 1 g (1.68 mmol) of mesoporphyrin-IX-dimethyl ester is suspended in a sealing tube in 300 ml of melted 1,5- diaminopentane and 200 ml of absolute pyridine. After covering with nitrogen, it is heated in a sealing tube for 3 days to 150° C. It is concentrated by evaporation in a medium high vacuum, the residue is mixed with 500 ml of diethyl ether, the precipitated solid is filtered off and rewashed with plenty of diethyl ether. The crude product is purified by recrystallization from pyridine/diethyl ether.

Yield: 932 mg (75.5% of theory) of reddish brown powder
Analysis (relative to the anhydrous substance): C 71.90 H 8.50 N 15.24 0 4.35 Cld. C 71.92 H 8.35 N 14.99 b) N,N'-Bis[16-carboxy-7-oxo-9,12-bis-(carboxymethyl)-15-(ethoxycarboxymethyl)-6,9, 12, 15-tetraazahexadecyl]-mesoporphyrin-IX-13,17-diamide 806.8 mg (2 mmol) of 3-ethoxy-carbonylmethyl-6-[2(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 mmol) of triethylamine and 735 mg (1 mmol) of N,N'-bis-(5-aminopentyl)-mesoporphyrin-IX-13,17-diamide (example 5a) are added and the resulting reaction mixture is stirred for 3 days at room temperature. After completion of the reaction, it is filtered, the solvent is removed in a vacuum and the remaining oil is triturated with 500 ml of diethyl ether. The precipitated solid is filtered off and washed with diethyl ether and hexane. For purification, it is chromatographed on silica gel RP-18 (Eluent: tetrahydrofuran/$H_2O$; tetrahydrofuran: 0–30%).

Yield: 1.31 g (85.0% of theory) of reddish brown powder
Analysis (relative to the anhydrous substance): C 59.21 H 7.32 N 12.72 O 20.75 Cld. C 59.00 H 7.51 N 12.47 c) N,N'-Bis[16-carboxylato-7-oxo-9,12-bis-(carboxylatomethyl)-15-(ethoxycarboxymethyl)-6,9,12,15-tetraazahexadecyl]-mesoporphyrin-IX-13,17-diamide, digadolinium complex 1.54 g (1 mmol) of the ligand produced in example 5b is dissolved in 400 ml of water. By addition of 2 n aqueous sodium hydroxide solution, it is adjusted to pH 7 and alternately 894.2 mg (2.2 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 (Eluent: tetrahydrofuran/$H_2O$; tetrahydrofuran: 0–30%).

Yield: 1.26 g (68.1% of theory) of reddish brown powder
Analysis (relative to the anhydrous substance): C 49.34 H 5.77 N 10.60 Gd 17.00 O 17.29 Cld. C 49.08 H 6.02 N 10.41 Gd 16.73 d) N,N'-Bis[16-carboxylato-7-oxo-9,12,15-tris-(carboxylatomethyl)-6,9,12,15-tetraazahexadecyl]-mesoporphyrin-IX-13,17-diamide, digadolinium complex, disodium salt 1.54 g (1 mmol) of the ligand produced in example 5b is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7 with concentrated hydrochloric acid and, as described in example 5c, complexed, worked up and purified with 894.2 mg (2.2 mmol) of gadolinium acetate tetrahydrate.

Yield: 1.49 g (81.1% of theory) of reddish brown powder
Analysis (relative to the anhydrous substance): 47.05 H 5.26 N 10.67 Gd 17.11 Na 2.50 O 17.11 Cld. C 39.87 H 5.45 N 10.38 Gd 17.01 Na 2.73

EXAMPLE 6 a) N,N'-Bis-(4-aminomethylbenzyl)-mesoporphyrin-IX-13,17-diamide 1 g (1.68 mmol) of mesoporphyrin-IX-dimethyl ester is suspended in a sealing tube in 300 ml of melted p-xylylenediamine and 200 ml of absolute pyridine. After covering with nitrogen, the reaction mixture is stirred for 3 days at 150° C. After completion of the reaction, the pyridine and the excess of p-xylylenediamine are distilled off in a medium-high vacuum and the residue is repeatedly recrystallized from pyridine/diethyl ether.

Yield: 921 mg (68.3% of theory) of reddish brown powder
Analysis (relative to the anhydrous substance): C 74.78 H 7.28 N 13.95 O 3.98 Cld. C 74.51 H 7.15 N 13.78 b) N,N'-Bis{4-[12-carboxy-3-oxo-5,8-bis-(carboxymethyl)-11-(ethoxycarboxymethyl)-2,5,8,11-tetraazadodecyl]benzyl}-mesoporphyrin-IX-13,17-diamide 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 mmol) of triethylamine and 803 mg (1 mmol) of N,N'-bis-(4-aminomethylbenzyl)-mesoporphyrin-IX-13,17-diamide (example 6a) are added and the resulting reaction mixture is stirred for 3 days at room temperature. After completion of the reaction, it is filtered, the solvent is removed in a vacuum and the remaining oil is triturated with 500 ml of diethyl ether. The precipitated solid is filtered off and washed with diethyl ether and hexane. For purification, it is chromatographed on silica gel RP-18 (Eluent: tetrahydrofuran/$H_2O$; tetrahydrofuran: 0–30%).

Yield: 923 mg (57.3% of theory) of reddish brown powder
Analysis (relative to the anhydrous substance): C 61.18 H 6.76 N 12.18 0 19.88 Cld. C 61.02 H 6.92 N 11.98 c) N,N'-Bis{4-[12-carboxy-3-oxo-5,8-bis-(carboxylatomethyl)-11-(ethoxycarboxymethyl)-2,5,8,11-tetraazadodecyl]benzyl}-mesoporphyrin-IX-13,17-diamide, digadolinium complex 1.61 g (1 mmol) of the ligand produced in example 6b is dissolved in 400 ml of water. By addition of 2 n aqueous sodium hydroxide solution, it is adjusted to pH 7 and alternately 894.2 mg (2.2 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 (Eluent: tetrahydrofuran/$H_2O$; tetrahydrofuran: 0–30%).

Yield: 985 mg (51.3% of theory) of reddish brown powder
Analysis (relative to the anhydrous substance): C 51.34 H 5.36 N 10.22 Gd 16.39 0 16.68 Cld. C 51.08 H 5.47 N 9.91 Gd 16.22 d) N,N'-Bis{4-[12-carboxylato-3-oxo-5,8,11-tris-(carboxylatomethyl)-2,5,8,11-tetraazadodecyl]benzyl}-mesoporphyrin-IX-13,17-diamide, digadolinium complex, disodium salt 1.61 g (1 mmol) of the ligand produced in example 6b is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7 with concentrated hydrochloric acid and, as described in example 6c, complexed, worked up and purified with 894.2 mg (2.2 mmol) of gadolinium acetate tetrahydrate.

Yield: 1.23 g (64.5% of theory) of reddish brown powder

Analysis (relative to the anhydrous substance): C 49.15 H 4.87 N 10.29 Gd 16.50 Na 2.41 O 16.79 Cld. C 48.98 H 4.95 N 10.12 Gd 16.31 Na 2.53

EXAMPLE 7 a) N,N'-Bis-butyl-mesoporphyrin-IX-13,17-diamide 1 g (1.68 mmol) of mesoporphyrin-IX-dimethyl ester is suspended in a sealing tube in 100 ml of absolute pyridine and 300 ml of n-butylamine. It is covered with nitrogen and the reaction mixture is heated for 3 days to 150° C. After completion of the reaction, it is concentrated by evaporation in a vacuum, the residue is taken up in 500 ml of chloroform, washed three times with 100 ml of 10% aqueous citric acid, three times with 100 ml of saturated sodium bicarbonate solution, dried on sodium sulfate and the solvent is removed in a vacuum. The purification of the amide takes place by chromatography on aluminum oxide (Eluent: chloroform/methanol 99:1)

Yield: 1.03 g (90.5% of theory) of violet powder

Analysis (relative to the anhydrous substance): C 74.52 H 8.34 N 12.41 O 4.73 Cld. C 74.28 H 8.44 N 12.32 b) 3,8-Diethyl-2,7,12,18-tetramethyl-13,17-bis(n-butylaminopropyl)-porphyrin 677 mg (1 mmol) of N,N'-bis-butyl-mesoporphyrin-IX-13,17-diamide (example 7a) is dissolved in 150 ml of absolute tetrahydrofuran under nitrogen atmosphere. It is mixed with 350 mg (16.1 mmol) of lithium borohydride, 2 ml of trimethylsilyl chloride and the resulting reaction mixture is stirred for 3 days at room temperature. After completion of the reaction, 20 ml of methanol and then 200 ml of water are instilled, it is adjusted to pH 1 with 2 molar hydrochloric acid, stirred for 0.5 hour, adjusted to pH 13 with 2 molar aqueous sodium hydroxide solution and stirred again for 0.5 hour. The reaction product is extracted three times with 100 ml of chloroform and the organic phase is dried on sodium sulfate. The purification of the amine takes place by chromatography on silica gel (Eluent: chloroform/methanol; methanol 0–50%).

Yield: 362 mg (55.8% of theory) of violet powder

Analysis (relative to the anhydrous substance): C 77.73 H 9.32 N 12.95 Cld. C 77.48 H 9.30 N 12.76 c) 3,8-Diethyl-2,7,12,18-tetramethyl-13,17-bis[4,7,10,13-tetraaza-4-butyl-5-oxo-7,10,13-tris(carboxymethyl)-13-ethoxycarboxymethyl-tridecyl]-porphyrin 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 -mmol) of triethylamine and 649 mg (1 mmol) of 3,8-diethyl-2,7,12,18-tetramethyl-13,17-bis(n-butylaminopropyl)-porphyrin (example 7b) are added and the resulting reaction mixture is stirred for three days at room temperature. After completion of the reaction, it is filtered, the solvent is removed in a vacuum and the remaining oil is triturated with 500 ml of diethyl ether. The precipitated solid is filtered off and washed with diethyl ether and n-hexane. For purification, it is chromatographed on silica gel RP-18 (Eluent: H$_2$O/tetrahydrofuran; tetrahydrofuran: 0–30%).

Yield: 1.05 g (72.1% of theory) of reddish brown powder

Analysis (relative to the anhydrous substance): C 61.05 H 7.62 N 11.55 O 19.78 Cld. C 60.89 H 7.72 N 11.31 d) 3,8-Diethyl-2,7,12,18-tetramethyl-13,17-bis-[4,7,10,13-tetraaza-4-butyl-5-oxo-7,10,13-tris(carboxylatomethyl)-13-ethoxycarboxymethyl-tridecyl]-porphyrin, digadolinium complex 1.46 g (1 mmol) of the ligand produced in example 7c is dissolved in 400 ml of water. By addition of two molar sodium hydroxide solution, it is adjusted to pH 7 and alternately 894.2 mg (2.2 mmol) of gadolinium acetate tetrahydrate and two molar sodium hydroxide solution are added in portions, so that the pH of the reaction mixture always fluctuates between 6.8 and 7.2. After all gadolinium acetate has been added, it is stirred overnight at room temperature. For working-up, the solvent is removed in a vacuum and the residue is chromatographed on silica gel RP-18 (Eluent: H$_2$O/tetrahydrofuran; tetrahydrofuran: 0–30%).

Yield: 721 mg (40.9% of theory) of reddish brown powder

Analysis (relative to the anhydrous substance): C 50.38 H 5.94 N 9.53 Gd 17.83 O 16.32 Cld. C 50.02 H 5.99 N 9.38 Gd 17.73 e) 3,8-Diethyl-2,7,12,18-tetramethyl-13,17-bis[4,7,10,13-tetraaza-4-butyl-5-oxo-7,10,13,13-tetra(carboxylatomethyl)-tridecyl]-porphyrin, digadolinium complex, disodium salt 1.46 g (1 mmol) of the ligand produced in example 7c is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7.0 with concentrated hydrochloric acid and, as described in example 7d, complexed, worked up and purified with 894.2 mg (2.2 mmol) of gadolinium acetate tetrahydrate.

Yield: 1.32 g (75.3% of theory) of reddish brown powder

Analysis (relative to the anhydrous substance): C 47.99 H 5.41 N 9.59 Gd 17.95 Na 2.62 O 16.44 Cld. C 47.76 H 5.63 N 9.31 Gd 17.81 Na 2.79

EXAMPLE 8 a) N,N'-Bis-benzyl-mesoporphyrin-IX-13,17-diamide 1 g (1.68 mmol) of mesoporphyrin-IX-dimethyl ester is refluxed in 500 ml of benzylamine under nitrogen atmosphere for 48 hours. After completion of the reaction, it is concentrated by evaporation in a vacuum, the residue is taken up in 500 ml of chloroform, the organic phase is washed three times with 150 ml of 5% aqueous citric acid, dried on sodium sulfate and concentrated by evaporation in a vacuum. It is crystallized from chloroform/methanol.

Yield: 920 mg (73.5% of theory) of red violet powder

Analysis (relative to the anhydrous substance): C 77.39 H 7.04 N 11.28 Cld. C 77.41 H 6.93 N 11.42 b) 3,8-Diethyl-2,7,12,18-tetramethyl-13,17-bis (benzylaminopropyl)-porphyrin 745 mg (1 mmol) of N,N'-bis-benzyl-mesoporphyrin-13,17-diamide is dissolved in 150 ml of tetrahydrofuran under nitrogen atmosphere. It is mixed with 350 mg (16.1 mmol) of lithium borohydride, 2 ml of trimethylsilyl chloride and the resulting reaction mixture is stirred for 3 days at room temperature. After completion of the reaction, 20 ml of methanol and then 200 ml of water are instilled, it is adjusted to pH 1 with 2 molar hydrochloric acid, stirred for 0.5 hour, adjusted to pH 13 with 2 molar sodium hydroxide solution and stirred again for 0.5 hour. The reaction product is extracted three times with 100 ml of chloroform and the organic phase is dried on sodium sulfate. The purification of the amine takes place by chromatography on silica gel (Eluent: chloroform/methanol; methanol 0–50%).

Yield: 425 mg (59.3% of theory) of red violet powder

Analysis (relative to the anhydrous substance): C 80.41 H 7.87 N 11.72 Cld. C 80.20 H 7.92 N 11.45 c) 3,8-Diethyl-2,7,12,18-tetramethyl-13,17-bis[4,7,10,13-tetraaza-4-benzyl-5-oxo-7,10,13-tris(carboxymethyl)-13-ethoxycarboxymethyl-tridecyl]-porphyrin 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is covered with nitrogen, 1.01 g (10 )mmol) of triethylamine and 717 mg (1 mmol) of 3,8-diethyl-2,7,12,18-tetramethyl-13,17-bis (benzylaminopropyl)porphyrin (example 8b) are added and the resulting reaction mixture is stirred for three days at room temperature. After completion of the reaction, it is filtered, the solvent is removed in a vacuum and the remaining oil is triturated with 500 ml of diethyl ether. The precipitated solid is filtered off and washed with diethyl ether and n-hexane. For purification, it is chromatographed on silica gel RP-18 (Eluent: $H_2O$/tetrahydrofuran; tetrahydrofuran: 0–30%).

Yield: 1.25 g (82% of theory) of reddish brown powder

Analysis (relative to the anhydrous substance): C 63.06 H 7.01 N 11.03 O 18.90 Cld. C 62.89 H 7.14 N 11.18 d) 3,8-Diethyl-2,7,12,18-tetramethyl-13,17-bis[4,7,10,13-tetraaza-4-benzyl-5-oxo-7,10,13-tris(carboxylatomethyl)-13-ethoxycarboxymethyl-tridecyl]-porphyrin, digadolinium complex 1.52 g (1 mmol) of the ligand produced in example 8c is dissolved in 400 ml of water. By addition of two molar sodium hydroxide solution, it is adjusted to pH 7 and alternately 89,4.2 mg (2.2 mmol) of gadolinium acetate tetrahydrate and two molar sodium hydroxide solution are added in portions, so that the pH of the reaction mixture always fluctuates between 6.8 and 7.2. After all gadolinium acetate has been added, it is stirred overnight at room temperature. For working-up, the solvent is removed in a vacuum and the residue is chromatographed on silica gel RP-18 (Eluent: $H_2O$/tetrahydrofuran; tetrahydrofuran: 0–30%).

Yield: 1.01 g (55.1% of theory) of reddish brown powder

Analysis (relative to the anhydrous substance): C 52.44 H 5.50 N 9.17 Gd 17.16 O 15.72 Cld. C 52.17 H 5.81 N 9.03 Gd 17.02 e) 3,8-Diethyl-2,7,12,18-tetramethyl-13,17-bis[4,7,10,1:3-tetraaza-4-benzyl-5-oxo-7,10,13,13-tetra (carboxylatomethyl)-tridecyl]-porphyrin, digadolinium complex, disodium salt 1.52 g (1 mmol) of the ligand produced in example 8c is dissolved in 400 ml of water. By addition of 10 molar aqueous sodium hydroxide solution, it is adjusted to pH 13 and stirred for 5 hours at room temperature. After completion of the saponification of the ester groups, it is adjusted to pH 7 with concentrated hydrochloric acid and, as described in example 8d, complexed, worked up and purified with 894.2 mg (2.2 mmol) of gadolinium acetate tetrahydrate.

Yield: 1.12 g (61.5% of theory) of reddish brown powder

Analysis (relative to the anhydrous substance): C 50.15 H 4.98 N 9.23 Gd 17.28 Na 2.53 O 15.82 Cld. C 50.02 H 4.99 N 9.05 Gd 17.03 Na 2.68

EXAMPLE 9 a) 10-[(2,6,7-Trihydroxy-4-oxa-heptyl]-1,4,7-tris-carboxymethyl-1,4,7,10-tetraazacyclododecane 19.56 g (103.92 mmol) of 2,2-dimethyl-4-(2',3'-epoxy)-propoxy-methyl-1,3-dioxolane and 10 g (28.86 mmol) of 1,4,7-triscarboxymethyl-1,4,7,10-tetraazacyclododecane (=DO3A) are dissolved in a mixture of 50 ml of dioxane/80 ml of water, and the pH is brought to pH 10 with 6N potassium hydroxide solution. It is stirred for 24 hours at 70° C. It is evaporated to dryness, the residue is taken up with 200 ml of water/50 ml of methanol and extracted twice with 100 ml of tert.-butyl-methyl ether. The aqueous solution is adjusted to pH 3 with 5N hydrochloric acid and evaporated to dryness. The residue is boiled out (extracted) with 200 ml of methanol/80 ml of dichloromethane. It is cooled in an ice bath and filtered from the precipitated potassium chloride. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed phase column (RP-18/mobile solvent, gradient from water/tetrahydrofuran). After concentration by evaporation of the main fraction, 10.13 g (71% of theory) of a strongly hygroscopic, vitreous solid is obtained.

Analysis (relative to the anhydrous substance): C 48.57 H 7.74 N 11.33 Cld. C 48.46 H 7.81 N 11.24 b) Gd-complex of 10-(2,6,7-trihydroxy-4-oxa-heptyl)-1,4,7-tris-carboxymethyl-1,4,7,10-tetraazacyclododecane 8.56 g (17.3 mmol) of the title compound from example 9a is dissolved in 50 ml of deionized water and 3.13 g (8.65 mmol) of gadolinium oxide is added. It is heated for 3 hours to 90° C. The cooled solution is stirred for one hour with 3 ml of acidic ion exchanger (AMB 252c) and 3 ml of weakly basic exchanger (IRA 67). It is filtered off from the exchanger and the filtrate freeze-dried.

Yield: 11.0 g (98% of theory) of a colorless amorphous powder.

Analysis (relative to the anhydrous substance): C 37.03 H 5.44 N 8.64 Gd 24.24 Cld.

C 37.00 H 5.51 N 8.57 Gd 24.18

The corresponding yttrium complex of 10-(2,6,7-trihydroxy-4-oxa-heptyl)-1,4,7-tris-carboxymethyl-1,4,7,10-tetraazacyclododecane is obtained analogously with yttrium oxide.

c) N,N'-Bis{4,7,10-tris(carboxylatomethyl)-1,4,7,10-tetraazacyclodecyl}-5-hydroxy-3-oxa-hexylamino}-mesoporphyrin-IX-13,17-diamide, digadolinium complex 3.89 g (6 mmol) of the Gd complex from example 9b is dissolved in 40 ml of methanol, mixed with 2.57 g (12 mmol) of sodium periodate and stirred up for 4 hours with exclusion of light. Then, it is filtered from the undissolved and the filtrate is freeze-dried. The residue is mixed with 500 ml of absolute dimethylformamide. It is covered with nitrogen, 6.06 g (60 mmol) of triethylamine and 1.78 g (3 mmol) of mesoporphyrin-IX-13,17-dihydrazide are added and it is allowed to stir for :3 days at room temperature. It is evaporated to dryness in a vacuum, the residue is mixed with 75 ml of buffer of pH 9.0 (Riedel de Haen, Borax/HCl), 1.13 g (18 mmol) of sodium cyanoborohydride is added and allowed to stir for 6 more days under nitrogen at room temperature. 2.8 g (52% of theory) of a reddish brown powder is obtained after chromatography of the neutral solution on silica gel RP-18.

Analysis (relative to the anhydrous substance): C 48.20 H 5.73 N 12.49 Gd 17.52 Cld. C 48.38 H 5.90 N 12.27 Gd 17.63

The di-yttrium complex is obtained analogously from the yttrium complex (example 9b).

d) N,N'-Bis{4,7,10-tris(carboxylatomethyl)-1,4,7,10-tetraazacyclododecyl }-5-hydroxy-3-oxahexyl-(1'-oxo-3'-oxa-4'-carboxylatobutyl)-amino}-mesoporphyrin-IX-13,17-diamide, digadolinium complex, disodium salt 2.5 g (1.41 mmol) of the title compound from example 9c is dissolved in 200 ml of N,N-dimethylformamide and 10 ml of pyridine is added. Then, 3.48 g (30 mmol) of diglycolic acid anhydride is added and stirred for 4 days at room temperature. It is evaporated to dryness in a vacuum, the residue is taken up with 20 ml of 20% aqueous acetic acid and again evaporated to dryness. The residue is chromatographed on silica gel RP-18. The main fractions are combined and evaporated to dryness. The residue is dissolved in 200 ml of water and the pH of the solution is adjusted to pH 7.2 with 0.1N sodium hydroxide solution. The solution is filtered and the filtrate dried. 2.17 g (75% of theory) of a reddish brown powder is obtained.

Analysis (relative to the anhydrous substance): C 45.74 H 5.41 N 10.94 Gd 15.35 Na 2.24 Cld. C 45.51 H 5.60 N 10.72 Gd 15.14 Na 2.01

EXAMPLE 10 a) 3,8-Bis-(hydroxymethyl)-deuteroporphyrin-IX-dimethyl ester 1.00 g (1.67 mmol) of 3,8-diformyl-deuteroporphyrin-IX-dimethyl ester (H. Fischer, K. O. Deilmann, Hoppe Seyler's Z. phys.Chem. 280, 186–216 (1944)) is dissolved in a mixture of 700 ml chloroform and 300 ml of methanol. The solution is cooled to 0C and mixed with stirring in portions with 1.00 g (26.43 mmol) of sodium borohydride. The batch is allowed to warm to room temperature, neutralized with semiconcentrated acetic acid and evaporated to dryness in a vacuum. The residue is taken up in methylene chloride, shaken out with saturated sodium bicarbonate solution, dried on sodium sulfate, filtered, concentrated by evaporation and recrystallized from methylene chloride/diethyl ether.

Yield: 0.92 g (92% of theory) of reddish brown powder

Analysis (relative to the anhydrous substance): C 68.21 H 6.40 N 9.36 O 16.03 Cld. C 68.01 H 6.35 N 9.22 b) 3,8-Bis-(methoxymethyl)-deuteroporphyrin-IX-dimethyl ester 0.90 g (1.44 mmol) of 3,8-bis-(hydroxymethyl)-deuteroporphyrin-IX-dimethyl ester (example b1a) is refluxed in a mixture of 40 ml of orthoformic acid-trimethyl ester, 40 ml of methanol and 8 ml of sulfuric acid for 2 hours. After cooling, the solution is neutralized with sodium bicarbonate, taken up in methylene chloride and washed with water. After drying on sodium sulfate, filtering and concentration by evaporation, the solid residue is recrystallized from methylene chloride/diethyl ether.

Yield: 0.78 g (86% of theory) of reddish brown powder

Analysis (relative to the anhydrous substance): C 68.90 H 6.75 N 8.94 O 15.32 Cld. C 68.81 H 6.71 N 8.85 c) N,N'-Bis-(2-aminoethyl)-3,8-bis-(methoxymethyl)-deuteroporphyrin-IX-13,17-diamide 0.70 g (1.12 mmol) of 3,8-bis-(methoxymethyl)-deuteroporphyrin-IX-dimethyl ester (example 10b) is heated in an autoclave in a mixture of 80 ml of pyridine and 20 ml of 1,2-diaminoethane after covering with nitrogen for 24 hours to 150° C. The batch is evaporated to dryness and the solid crude product is purified by recrystallization from pyridine/diethyl ether.

Yield: 0.63 g (83% of theory) of reddish brown powder

Analysis (relative to the anhydrous substance): C 66.84 H 7.38 N 16.41 O 9.37 Cld. C 66.68 H 7.11 N 16.42 d) N,N'-Bis-[13-carboxy-4-oxo-6,9-bis-(carboxymethyl)-12-(ethoxycarbonylmethyl)-3,6,9,12-tetraazatridecyl]-3,8-bis-(methoxymethyl)-deuteroporphyrin-IX-13,17-diamide 0.71 g (1.76 mmol) of 3-ethoxy-carbonylmethyl-6-[2-(2,6-dioxomorpholino)-ethyl]-3,6-diazaoctanedioic acid (DTPA-monoanhydride-monoethyl ester) is suspended in 100 ml of anhydrous dimethylformamide. It is covered with nitrogen, 0.89 g (8.80 mmol) of triethylamine and 0.60 g (0.88 mmol) of N,N'-bis-(2-aminoethyl)-3,8-bis-(methoxymethyl)-deuteroporphyrin-IX-13,l17-diamide (example 10c) are added and stirred for 3 days at room temperature. After filtering and concentration by evaporation in a vacuum, the residue is chromatographed on silica gel RP-18 with water/tetrahydrofuran and evaporated to dryness in a vacuum.

Yield: 1.09 g (83% of theory) of reddish brown powder

Analysis (relative to the anhydrous substance): C 56.44 H 6.77 N 13.16 O 23.63 Cld. C 56.18 H 6.63 N 13.27 e) N,N'-Bis-[13-carboxylato-4-oxo-6,9-bis-(carboxylatomethyl)-12-(ethoxycarbonylmethyl)-3,6,9,12-tetraazatridecyl]-3,8-bis-(methoxymethyl)-deuteroporphyrin-IX-13,17-diamide, digadolinium complex 1.00 g (0.67 mmol) of the ligand produced in example 10d) is dissolved in 250 ml of water. By addition of 2 n aqueous sodium hydroxide solution, it is adjusted to pH 7.0, and 0.60 g (1.4Z7 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum, the residue is chromatographed on silica gel RP-18 with water/tetrahydrofuran and evaporated to dryness in a vacuum.

Yield: 0.87 g (72% of theory) of reddish brown powder

Analysis (relative to the anhydrous substance): C 46.76 H 5.27 Gd 17.49 N 10.91 O 19.58 Cld. C 46.54 H 5.23 Gd 17.42 N 10.75 f) N,N'-Bis-(13-carboxylato-4-oxo-6,9,12-tris-(carboxylatomethyl)-3,6,9,12-tetraazatridecyl]-3,8-bis-(methoxymethyl)-deuteroporphyrin-IX-13,17-diamide, digadolinium complex, disodium salt 1.00 g (0.67 mmol) of the ligand produced in example 10d is dissolved in 200 ml of water. By addition of 10n aqueous sodium hydroxide solution, it is adjusted to pH 13 and stirred for 5 hours at room temperature. After completion of the saponification of the ester, it is adjusted to pH 7 with concentrated hydrochloric acid and, as described in example 10e, complexed, worked up and purified with 0.60 g (1.47 mmol) of gadolinium acetate tetrahydrate.

Yield: 1.01 g (84% of theory)

Analysis (relative to the anhydrous substance): C 44.39 H 4.74 N 10.98 Gd 17.61 Na 2.57 O 19.71 Cld. C 44.17 H 4.68 N 10.89 Gd 17.65 Na 2.63

EXAMPLE 11 a) N-(2-aminoethyl)-3,8-bis-(mthoxymethyl)-deuteroporphyrin-IX-monoamide-monoethyl ester (isomeric mixture)

0.70 g (1.12 mmol) of 3,8-bis-(methoxymethyl)-deuteroporphyrin-IX-dimethyl ester (example 10b) is heated in an autoclave for 12 hours to 150° C. in a mixture of 90 ml of pyridine and 10 ml of 1,2-diaminoethane after covering with nitrogen. The batch is concentrated by evaporation and the solid crude product is purified by recrystallization from pyridine/diethyl ether.

Yield: 0.56 g (86% of theory) of reddish brown powder b) N-(2-aminoethyl)-3,8-bis-(methoxymethyl)-deuteroporphyrin-IX-monoamide-monosodium salt (isomeric mixture)

0.50 g (0.75 mmol) of the compound produced in example 11a is stirred in a mixture of 100 ml of pyridine and 100 ml of 1 n sodium hydroxide solution for two hours at 50° C.; then it is concentrated by evaporation in a vacuum. The residue is suspended in 100 ml of water, the suspension is neutralized with 0.1 n hydrochloric acid, the precipitate is suctioned off, washed with water and dried in a vacuum on phosphorus pentoxide.

Yield: 0.41 g (81% of theory) of reddish brown powder c) N-[13-carboxy-4-oxo-6,9-bis-(carboxymethyl)-12-(ethoxycarbonylmethyl)-3,6,9,12-tetraazatridecyl]-3,8-bis-(methoxymethyl)-deuteroporphyrin-IX-monoamide-sodium salt (isomeric mixture)

0.24 g (0.60 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 80 ml of anhydrous dimethylformamide. It is covered with nitrogen, 0.30 g (3.00 mmol) of triethylamine and 0.40 g (0.60 mmol) of the compound produced in example lib are added and stirred for 3 days at room temperature. After filtering and concentration by evaporation in a vacuum, the residue is suspended in a little water, dissolved by addition of 2 n sodium hydroxide solution at pH 7.2, chromatographed on silica gel RP-18 with water/tetrahydrofuran and the eluate is evaporated to dryness in a vacuum.

Yield: 0.37 g (58% of theory) of reddish brown powder
Analysis (relative to the anhydrous substance): C 58.58 H 6.43 N 11.82 Na 2.16 O 21.01 Cld. C 58.49 H 6.40 N 11.58 Na 2.35 d) N-[13-Carboxylato-4-oxo-6,9-bis-(carboxylatomethyl)-12-(ethoxycarbonylmethyl)-3,6,9,12-tetraazatridecyl]-3,8-bis-(methoxymethyl)-deuteroporphyrin-IX-monoamide, gadolinium complex, sodium salt (isomeric mixture)

0.35 g (0.33 mmol) of the ligand produced in example 11c is dissolved in 100 ml of water. By addition of 2 n aqueous sodium hydroxide solution, it is adjusted to pH 7.0, and 0.15 g (0.36 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum, the residue is chromatographed on silica gel RP-18 with water/tetrahydrofuran and the eluate is evaporated to dryness in a vacuum.

Yield: 0.33 g (81% of theory) of reddish brown powder
Analysis (relative to the anhydrous substance): C 51.18 H 5.37 N 10.33 Na 1.88 Gd 12.89 O 18.35 Cld. C 50.88 H 5.35 N 10.24 Na 1.91 Gd 12.90 e) N-[13-Carboxylato-4-oxo-6,9,12-tris-(carboxylatomethyl)-3,6,9,12-tetraazatridecyl]-3,8-bis-(methoxymethyl)-deuteroporphyrin-IX-monoamide, digadolinium complex, disodium salt (isomeric mixture)

0.35 g (0.33 mmol) of the ligand produced in example 12c is dissolved in 100 ml of water. By addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 11d, complexed, worked up and purified with 0.15 g (0.36 mmol) of gadolinium acetate tetrahydrate.

Yield: 0.33 g (83% of theory) of reddish brown powder
Analysis (relative to the anhydrous substance): C 49.46 H 4.98 N 10.38 Na 3.79 Gd 12.95 O 18.45 Cld. C 49.35 H 5.06 N 10.27 Na 3.85 Gd 12.89

EXAMPLE 12 a) Manganese(III)-[N,N'-bis-(2-aminoethyl)-3,8-bis-(methoxymethyl)-deuteroporphyrin-IX-13,17-diamide]-acetate 0.60 g (0.88 mmol) of the compound produced in example 10c is refluxed with 3.00 g of manganese(II)-acetate for one hour in 120 ml of acetic acid. Then, it is concentrated by evaporation in a vacuum, the residue is suspended in water, filtered off and washed with water. The dried crude product is recrystallized from pyridine/diethyl ether.

Yield: 0.64 g (91% of theory) of reddish brown powder
Analysis (relative to the anhydrous substance): C 60.45 H 6.47 Mn 6.91 N 14.10 O 12.08 Cld. C 60.18 H 6.51 Mn 6.90 N 13.97 b) Manganese(III)-{N,N'-bis-[13-carboxy-4-oxo-6,9-bis-(carboxymethyl)-12-(ethoxycarbonylmethyl)-3,6,9,12-tetraazatridecyl]-3,8-bis-(methoxymethyl)-deuteroporphyrin-IX-13,17-diamide}-acetate 0.61 g (1.50 mmol) of 3-ethoxy-carbonylmethyl-6-[2-(2,6-dioxomorpholino)-ethyl]-3,6-diazaoctanedioic acid (DTPA-monoanhydridemonomethyl ester) is suspended in 100 ml of anhydrous dimethylformamide. It is covered with nitrogen, 0 76 g (7.50 mmol) of triethylamine and 0.60 g (0.75 mmol) of the compound produced in example 12a are added and stirred for 3 days at room temperature. After filtering and concentration by evaporation in a vacuum, the residue is chromatographed on silica gel RP-18 with water/tetrahydrofuran and the eluate is evaporated to dryness in a vacuum.

Yield: 1.01 g (84% of theory) of reddish brown powder
Analysis (relative to the anhydrous substance): C 54.00 H 6.36 Mn 3.43 N 12.24 0 23.98 Cld. C 53.79 H 6.31 Mn 3.11 N 12.03 c) Manganese(III)-{N,N'-bis-[13-carboxylato-4-oxo-6,9-bis-(carboxylatomethyl)-12-(ethoxycarbonylmethyl)-3,6,9,12-tetraazatridecyl]-3,8-bis-(methoxymethyl)-deuteroporphyrin-IX-13,17-diamide}-acetate, digadolinium complex 1.00 g (0.62 mmol) of the ligand produced in example 12b is dissolved in 250 ml of water. By addition of 2 n sodium hydroxide solution, it is adjusted to pH 7.0, and 0.55 g (1.36 mmol) of gadolinium acetate and 2 n sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum, the residue is chromatographed on silica gel RP-18 with water/tetrahydrofuran and the eluate is evaporated to dryness in a vacuum.

Yield: 0.85 g (72% of theory) of reddish brown powder
Analysis (relative to the anhydrous substance): C 45.28 H 5.01 N 10.27 Gd 16.47 Mn 2.88 O 20.10 Cld. C 45.07 H 4.88 N 10.16 Gd 16.51 Mn 2.80 d) Manganese(III)-{N,N'-bis-[13-carboxylato-4-oxo-6,9,12-tris-(carboxylatomethyl)-3,6,9,12-tetraazatridecyl]-3,8-bis-(methoxymethyl)-deuteroporphyrin-IX-13,17-diamide}-acetate, digadolinium complex, disodium salt 1.00 g (0.52 mmol) of the ligand produced in example 12b is dissolved in 250 ml of water. By addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 12c, complexed and purified with 0.47 g (1.15 mmol) of gadolinium acetate tetrahydrate.

Yield: 80 g (81% of theory)
Analysis (relative to the anhydrous substance): C 43.03 H 4.51 N 10.33 Na 2.42 Gd 16.57 Mn 2.89 O 20.2:3 Cld. C 42.88 H 4.36 N 10.30 Na 2.24 Gd 16.49 Mn 2.82

EXAMPLE 13 a) 3,8-Bis-(methoxymethyl)-deuteroporphyrin-IX-13,17-dihydrazide 1.00 g (1.60 mmol) of the compound produced in example 10b is dissolved in 80 ml of anhydrous pyridine under argon and mixed with 15 ml of hydrazine. After 3 days of stirring at room temperature, it is concentrated by evaporation in a vacuum, the residue is stirred in semiconcentrated aqueous hydrochloric acid and mixed with 6 n sodium hydroxide solution to adjust the pH to 7.0. The precipitate is filtered off, washed with water and recrystallized from pyridine/ether.

Yield: 0.81 g (81% of theory) of reddish brown powder
Analysis (relative to the anhydrous substance): C 65.16 H 6.75 N 17.88 O 10.21 Cld. C 64.87 H 6.62 N 17.64 b) N,N'-Bis-[11-carboxy-2-oxo-4,7-bis-(carboxymethyl)-10-(ethoxycarbonylmethyl)-1,4,7,10-tetraazaundecyl]-3,8-bis-(methoxymethyl)-deuteroporphyrin-IX-13,17-diamide 0.90 g (2.23 mmol) of 3-ethoxy-carbonylmethyl-6-[2,6-dioxomorpholino)-ethyl]-3,6-diazaoctanedioic acid (DTPA-monoanhydridemonoethyl ester) is suspended in 250 ml of anhydrous dimethylformamide. It is covered with nitrogen, 0.9 g (11.17 mmol) of triethylamine and 0.70 g (1.12 mmol) of the compound produced in example 13a are added and stirred for 3 days at room temperature. After filtering and concentration by evaporation in a vacuum, the residue is chromatographed on silica gel RP-18 with water/tetrahydrofuran and the eluate is evaporated to dryness.

Yield: 1.35 g (84% of theory) of reddish brown powder
Analysis (relative to the anhydrous substance): C 55.30 H 6.47 N 13.68 O 24.55 Cld. C 55.01 H 6.42 N 13.36 c) N,N'-Bis-[11-carboxylato-2-oxo-4,7-bis-(carboxylatomethyl)-10-(ethoxycarbonylmethyl)-1,4,7,10-tetraazaundecyl]-3,8-bis-(methoxymethyl)-deuteroporphyrin-IX-13,17-diamide, digadolinium complex 1.30 g (0.91 mmol) of the ligand produced in example 13b is dissolved in 250 ml of water. The pH is adjusted to 7.0 by addition of 2 molar aqueous sodium hydroxide solution and 0.80 g (2.00 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum, the residue is chromatographed on silica gel RP-18 with water/tetrahydrofuran and the eluate is evaporated to dryness.

Yield: 1.27 g (80% of theory) of reddish brown powder
Analysis (relative to the anhydrous substance): C 45.51 H 4.98 N 11.26 Gd 18.05 O 20.21 Cld. C 45.43 H 4.86 N 10.97 Gd 17.87 d) N,N'-Bis-[11-carboxylato-2-oxo-4,7,10-tris-(carboxylatomethyl)-1,4,7,10-tetraazaundecyl]-3,8-bis-(methoxymethyl)-deuteroporphyrin-IX-13,17-diamide, digadolinium complex, disodium salt 1.00 g (0.70 mmol) of the ligand produced in example 13b is dissolved in 200 ml of water. By addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 13c, complexed, worked up and purified with 0.62 g (1.53 mmol) of gadolinium acetate tetrahydrate.

Yield: 0.86 g (71% of theory) of reddish brown powder
Analysis (relative to the anhydrous substance): C 43.05 H 4.42 N 11.34 Na 2.65 Gd 18.18 O 20.35 Cld. C 42.88 H 4.31 N 11.12 Na 2.71 Gd 18.09

EXAMPLE 14 a) Zn-[3,8-bis-(1-propenyl)-deuteroporphyrin-IX-dimethyl ester]

2.48 g (6.69 mmol) of ethyltriphenylphosphoniumbromide in 600 ml of anhydrous tetrahydrofuran is mixed under argon at room temperature with a solution of 0.43 g (6.69 mmol) of n-butyllithium. After completion of the reaction, 2.00 g (3.04 mmol) of Zn-[3,8-diformyl-deuteroporphyrin-IX-dimethyl ester] (Kevin M. Smith, Eugene M. Fujinari, Keven C. Langry, Daniel W. Parish and Hani D. Tabba, J. Am. Chem. Soc. 105, 6638–6646 (1983) is added and stirred for two more hours. After addition of 30 ml of methanol, the solvent is substantially removed in a vacuum and the residue shaken out with methylene chloride and semiconcentrated aqueous sodium bicarbonate solution. The organic phase is dried on sodium sulfate, concentrated by evaporation and chromatographed on aluminum oxide (Merck, activity stages 2–3) with methylene chloride/methanol. The eluate is evaporated to dryness in a vacuum.

Yield: 1.78 g (86% of theory) of reddish brown powder
Analysis (relative to the anhydrous substance): C 66.91 H 5.91 N 8.21 Zn 9.58 O 9.38 Cld. C 66.62 H 5.79 N 8.07 Zn 9.55 b) 3,8-Bis-(n-propyl)-deuteroporphyrin-IX-dimethyl ether 1.70 g (2.49 mmol) of the compound produced in example 14a is catalytically hydrogenated under the conditions used for the production of mesoporphyrin-IX-dimethyl ester from protoporphyrin-IX-dimethyl ester (H. Muir and A. Neuberger, Biochem. J., 45, 163 (1949)) with simultaneous demetallization until the UV spectrum corresponds to the etio type and is worked up and recrystallized corresponding to these instructions in the literature.

Yield: 1.42 g (92% of theory) of reddish brown powder
Analysis (relative to the anhydrous substance): C 73.28 H 7.44 N 9.00 O 10.28 Cld. C 72.97 H 7.38 N 8.85 c) 3,8-Bis-(n-propyl)-deuteroporphyrin-IX-13,17-dihydrazide 1.40 g (2.25 mmol) of the compound produced in example 14b is dissolved in 110 ml of anhydrous pyridine under argon and mixed with 20 ml of hydrazine. After 3 days of stirring at 20° C., it is concentrated by evaporation in a vacuum, the residue is stirred in semiconcentrated aqueous hydrochloric acid and precipitated with 6 n sodium hydroxide solution by adjusting the pH to 7.0. The precipitate is filtered off, washed with water and recrystallized from pyridine/ether.

Yield: 1.25 g (89% of theory) of reddish brown powder
Analysis (relative to the anhydrous substance): C 69.43 H 7.44 N 17.99 O 5.38 Cld. C 69.19 H 7.37 N 17.65 d) N,N'-Bis-[11-carboxy-2-oxo-4,7-bis-(carboxymethyl)-10-(ethoxycarbonylmethyl)-1,4,7,10-tetraazaundecyl]-3,8-bis-(n-propyl)-deuteroporphyrin-IX-13,17-diamide 1.56 g (3.86 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 250 ml of anhydrous dimethylformamide. It is covered with nitrogen, 1.95 g (19.30 mmol) of triethylamine and 1.20 g (1.93 mmol) of the compound produced in example 14c are added and stirred for 3 days at room temperature. After filtering and concentration by evaporation in a vacuum, the residue is chromatographed on silica gel RP-18 with water/tetrahydrofuran and the eluate is evaporated to dryness in a vacuum.

Yield: 4.75 g (86% of theory) of reddish brown powder
Analysis (relative to the anhydrous substance): C 57.13 H 6.77 N 13.72 O 22.38 Cld. C 56.86 H 6.69 N 13.65 e) N,N'-Bis-[11-carboxylato-2-oxo-4,7-bis-(carboxylatomethyl)-10-(ethoxycarbonylmethyl)-1,4,7,10-tetraazaundecyl]-3,8-bis-(n-propyl)-deuteroporphyrin-IX-13,17-diamide, digadolinium complex 4.70 g (3.29 mmol) of the ligand produced in example 14d is dissolved in 1000 ml of water. After addition of 2 n aqueous sodium hydroxide solution, it is adjusted to pH 7.0, 2.94 g (7.24 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 with water/tetrahydrofuran. The eluate is evaporated to dryness in a vacuum.

Yield: 4.35 g (76% of theory) of reddish brown powder
Analysis (relative to the anhydrous substance): C 46.99 H 5.22 N 11.28 Gd 18.09 O 18.41 Cld. C 46.75 H 5.16 N 11.02 Gd 18.02 f) N,N'-Bis-[11-carboxylato-2-oxo-4,7,10-tris-(carboxylatomethyl)-1,4,7,10-tetraazaundecyl]-3,8-bis-X-(1-propyl)-deuteroporphyrin-IX-13,17-diamide, digadolinium complex, disodium salt 2.00 g (1.40 mmol) of the ligand produced in example 14d is dissolved in 200 ml of water. After addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 14e, complexed and purified with 1.36 g (3.08 mmol) of gadolinium acetate tetrahydrate.

Yield: 1.80 g (75% of theory) of reddish brown powder

Analysis (relative to the anhydrous substance): C 44.54 H 4.67 N 11.36 Gd 18.22 O 18.54 Cld. C 44.26 H 4.57 N 11.13 Gd 18.13

EXAMPLE 15 a) Zinc(II)-[3,8-bis-(1-butenyl)-deuteroporphyrin-IX-dimethyl ester]

2.58 g (6.69 mmol) of propyltriphenylphosphoniumbromide in 600 ml of anhydrous tetrahydrofuran is mixed under argon at room temperature with a solution of 0.43 g (6.69 mmol) of butyllithium. After completion of the reaction to the ylide, 2.00 g (3.04 mmol) of Zn-[3,8-diformyl-deuteroporphyrin-IX-dimethyl ester] (Kevin M. Smith, Eugene M. Fujinari, Kevin C. Langry, Daniel W. Parish and Hani D. Tabba, J. Am. Chem. Soc. 105, 6638–6646 (1983)) is added and stirred for two more hours. After addition of 30 ml of methanol, the solvent is substantially removed in a vacuum and the residue shaken out with methylene chloride and semiconcentrated aqueous sodium bicarbonate solution. The organic phase is dried on sodium sulfate, concentrated by evaporation and chromatographed on aluminum oxide (Merck, activity stages 2–3) with methylene chloride/methanol. The eluate is evaporated to dryness in a vacuum.

Yield: 1.75 g (81% of theory) of reddish brown powder

Analysis (relative to the anhydrous substance): C 67.65 H 62.44 N 7.89 Zn 9.20 O 9.01 Cld. C 67.41 H 62.27 N 7.63 Zn 9.15 b) 3,8-Bis-(n-butyl)-deuteroporphyrin-IX-dimethyl ester 1.6 g (2.25 mmol) of the compound produced in example 15a is catalytically hydrogenated under the conditions used for the production of mesoporphyrin-IX-dimethyl ester from protoporphyrin-IX-dimethyl ester (H. Muir and A. Neuberger, Biochem. J., 45, 163 (1949)) with simultaneous demetallization, until the UV spectrum corresponds to the etio type and is worked up and recrystallized corresponding to these instructions in the literature.

Yield: 1.39 g (95% of theory) of reddish brown powder

Analysis (relative to the anhydrous substance): C 73.82 H 7.74 N 8.61 O 9.83 Cld. C 73.55 H 7.62 N 8.48 c) 3,8-Bis-(n-butyl)-deuteroporphyrin-IX-13,17-dihydrazide 1.30 g (2.00 mmol) of the compound produced in example 15b is dissolved in 100 ml of anhydrous pyridine under argon and mixed with 20 ml of hydrazine. After 3 days of stirring at 20° C., it is concentrated by evaporation in a vacuum, the residue is stirred in semiconcentrated hydrochloric acid and precipitated with 6 n sodium hydroxide solution by adjusting the pH to 7.0. The precipitate is filtered off, washed with water and recrystallized from pyridine/ether.

Yield: 1.18 g (91% of theory) of reddish brown powder

Analysis (relative to the anhydrous substance): C 70.13 H 7.74 N 17.22 O 4.92 Cld. C 69.85 H 7.68 N 17.01 d) N,N'-Bis-[11-carboxy-2-oxo-4,7-bis-(carboxymethyl)-10-(ethoxycarbonylmethyl)-1,4,7,10-tetraazaundecyl]-3,8-bis-(n-butyl)-deuteroporphyrin-IX-13,17-diamide 1.24 g (3.07 mmol) of 3-ethoxy-carbonylmethyl-6-(2-(2,6-dioxomorpholino)-ethyl]-3,6-diazaoctanedioic acid (DTPA-monoanhydridemonoethyl ester) is suspended in 200 ml of anhydrous dimethylformamide. It is covered with nitrogen, 1.55 g (15.36 mmol) of triethylamine and 1.00 g (1.54 mmol) of the compound produced in example 15c are added and stirred for 3 days at room temperature. After filtering and concentration by evaporation in a vacuum, the residue is chromatographed on silica gel RP-18 with water/tetrahydrofuran. The eluate is evaporated to dryness in a vacuum.

Yield: 2.00 g (89% of theory) of reddish brown powder

Analysis (relative to the anhydrous substance): C 57.68 H 6.91 N 13.45 O 21.95 Cld. C 57.38 H 6.77 N 13.19 e) N,N'-Bis-[11-carboxylato-2-oxo-4,7-bis-(carboxylatomethyl)-10-(ethoxycarbonylmethyl)-1,4,7,10-tetraazaundecyl]-3,8-bis-(n-butyl)-deuteroporphyrin-IX-13,17-diamide, digadolinium complex 1.00 g (0.69 mmol) of the ligand produced in example 15d is dissolved in 200 ml of water. After addition of 2 n aqueous sodium hydroxide solution, it is adjusted to pH 7.0, 0.62 g (1.52 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 with water/tetrahydrofuran and the eluate is evaporated to dryness in a vacuum.

Yield: 0.87 g (71% of theory) of reddish brown powder

Analysis (relative to the anhydrous substance): C 47.61 H 5.36 N 11.10 Gd 17.81 O 18.12 Cld. C 47.65 H 5.51 N 11.23 Gd 17.71 f) N,N'-Bis-[11-carboxylato-2-oxo-4,7-tris-(carboxylatomethyl) -1,4,7,10-tetraazaundecyl]-3,8-bis-(n-butyl) -deuteroporphyrin-IX-13,17-diamide, digadolinium complex, disodium salt 1.00 g (0.69 mmol) of the ligand produced in example 15d is dissolved in 200 ml of water. After addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 15e, complexed and purified with 0.62 g (1.52 mmol) of gadolinium acetate tetrahydrate.

Yield: 0.88 g (73% of theory) of reddish brown powder

Analysis (relative to the anhydrous substance): C 45.20 H 4.83 N 11.18 Na 2.61 Gd 17.93 O 18.25 Cld. C 44.93 H 4.76 N 11.01 Na 2.52 Gd 17.82

EXAMPLE 16 a) Zinc(II)-[3,8-bis-(1-heptenyl)-deuteroporphyrin-IX-dimethyl ester]

2.86 g (6.69 mmol) of hexyltriphenylphosphoniumbromide in 600 ml of anhydrous tetrahydrofuran is mixed under argon at room temperature with a solution of 0.43 g (6.69 mmol) of butyllithium. After completion of the reaction to the ylide, 2.00 g (3.04 mmol) of Zn-[3,8-diformyldeuteroporphyrin-IX-dimethyl ester] (Kevin M. Smith, Eugene M. Fujinari, Kevin C. Langry, Daniel W. Parish and Hani D. Tabba, J. Am. Chem. Soc. 105, 6638–6646 (1983)) is added and stirred for two more hours. After addition of 30 ml of methanol, the solvent is substantially removed in a vacuum and shaken out with methylene chloride and semiconcentrated aqueous sodium bicarbonate solution. The organic phase is dried on sodium sulfate, concentrated by evaporation and chromatographed on aluminum oxide (Merck, activity stages 2–3) with methylene chloride/methanol. The eluate is evaporated to dryness in a vacuum.

Yield: 1.91 g (79% of theory) of reddish brown powder
Analysis (relative to the anhydrous substance): C 69.56 H 7.11 N 7.05 Zn 8.23 O 8.06 Cld. C 69.11 H 6.88 N 6.79 Zn 8.16 b) 3,8-Bis-(n-heptyl)-deuteroporphyrin-IX-dimethyl ester 1.50 g (1.89 mmol) of the compound produced in example 16a is catalytically hydrogenated under the conditions used for the production of mesoporphyrin-IX-dimethyl ester from protoporphyrin-IX-dimethyl ester (H. Muir and A. Neuberger, Biochem. J., 45, 163 (1949)) by simultaneous demetallization until the UV spectrum corresponds to the etio type and is worked up and recrystallized corresponding to these instructions in the literature.

Yield: 1.32 g (95% of theory) of reddish brown powder
Analysis (relative to the anhydrous substance): C 75.17 H 8.50 N 7.62 O 8.71 Cld. C 74.83 H 8.39 N 7.37 c) 3,8-Bis-(1-heptyl)-deuteroporphyrin-IX-13,17-dihydrazide 1.30 g (1.77 mmol) of the compound produced in example 16b is dissolved in 100 ml of anhydrous pyridine and mixed with 20 ml of hydrazine. After 3 days of stirring at 20° C., it is concentrated by evaporation in a vacuum, the residue is stirred in semiconcentrated aqueous hydrochloric acid and again precipitated with 6 n sodium hydroxide solution by adjusting the pH to 7.0. The precipitate is filtered off, washed with water and recrystallized from pyridine/ether.

Yield: 1.14 g (88% of theory) of reddish brown powder
Analysis (relative to the anhydrous substance): C 71.90 H 8.50 N 15.24 O 4.35 Cld. C 71.78 H 8.39 N 14.97 d) N,N'-Bis-[11-carboxy-2-oxo-4,7-bis-(carboxymethyl)-10-(ethoxycarbonylmethyl)-1,4,7,10-tetraazaundecyl]-3,8-bis-(n-heptyl)-deuteroporphyrin-IX-13,17-diamide 1.21 g (3.00 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 200 ml of anhydrous dimethylformamide. It is covered with nitrogen, 1.52 g (15.00 mmol) of triethylamine and 1.10 g (1.50 mmol) of the compound produced in example 16c are added and stirred for 3 days at room temperature. After filtering and concentration by evaporation in a vacuum, the residue is chromatographed on silica gel RP-18 with water/tetrahydrofuran and the eluate is evaporated to dryness in a vacuum.

Yield: 2.06 g (89% of theory) of reddish brown powder
Analysis (relative to the anhydrous substance): C 59.21 H 7.32 N 12.72 O 20.75 Cld. C 58.97 H 7.11 N 12.61 e) N,N'-Bis-[11-carboxylato-2-oxo-4,7-bis-(carboxylatomethyl)-10-ethoxycarbonylmethyl-1,4,7,10-tetraazaundecyl]-3,8-bis-(n-heptyl)-deuteroporphyrin-IX-13,17-diamide, digadolinium complex 1.00 g (0.65 mmol) of the ligand produced in example 16d is dissolved in 300 ml of water. After addition of 2 n aqueous sodium hydroxide solution, it is adjusted to pH 7.0, and 0.58 g (1.43 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum, the residue is chromatographed on silica gel RP-18 with water/tetrahydrofuran and the eluate is evaporated to dryness in a vacuum.

Yield: 0.87 g (72% of theory) of reddish brown powder
Analysis (relative to the anhydrous substance): C 49.34 H 5.77 N 10.60 Gd 17.00 O 17.29 Cld. C 49.07 H 5.68 N 10.42 Gd 16.89 f) N,N'-Bis-[11-carboxylato-2-oxo-4,7,10-tris-(carboxylatomethyl)-1,4,7,10-tetraazaundecyl]-3,8-bis-(n-heptyl)-deuteroporphyrin-IX- 13,17-diamide, digadolinium complex, disodium salt 1.00 g (0.65 mmol) of the ligand produced in example 16d is dissolved in 300 ml of water. After addition of 10 molar aqueous sodium hydroxide solution, it is adjusted to pH 13 and stirred for 5 hours at room temperature. After completion of the saponification of the ester, it is adjusted to pH 7.0 with concentrated hydrochloric acid and, as described in example 16e, complexed and purified with 0.58 g (1.43 mmol) of gadolinium acetate tetrahydrate.

Yield: 0.91 g (76% of theory) of reddish brown powder
Analysis (relative to the anhydrous substance): C 47.05 H 5.26 N 10.67 Na 2.49 Gd 17.11 O 17.41 Cld. C 46.86 H 5.07 N 10.42 Na 2.51 Gd 17.09

EXAMPLE 17 a) Zinc(II)-[3,8-bis-(2-phenylethenyl)-deuteroporphyrin-IX-dimethyl ester]

2.60 g (6.69 mmol) of benzyltriphenylphosphonium-chloride in 600 ml of anhydrous tetrahydrofuran is mixed under argon at room temperature with a solution of 0.43 g (6.69 mmol) of butyllithium. After completion of the reaction to the ylide, 2.00 g (3.04 mmol) of Zn-[3,8-diformyl-deuteroporphyrin-IX-dimethyl ester] (Kevin M. Smith, Eugene M. Fujinari, Kevin C. Langry, Daniel W. Parish and Hani D. Tabba, J. Am. Chem. Soc. 105, 6638–6646 (1983)) is added and stirred for two more hours. After addition of 30 ml of methanol, the solvent is substantially removed in a vacuum and the residue shaken out with methylene chloride and semiconcentrated aqueous sodium bicarbonate solution. The organic phase is dried on sodium sulfate, concentrated by evaporation, chromatographed on aluminum oxide (Merck, activity stages 2–3) with methylene chloride/methanol and the eluate is evaporated to dryness.

Yield: 2.23 g (91% of theory) of reddish brown powder
Analysis (relative to the anhydrous substance): C 71.51 H 5.50 N 6.95 Zn 8.11 O 7.94 Cld. C 71.24 H 5.39 N 6.68 Zn 8.06 b) Zinc(II)-[3,8-bis-(2-phenylethyl)-deuteroporphyrin-IX-dihydrazide]2.10 g (2.60 mmol) of the compound produced in example 17a is dissolved in 130 ml of pyridine and mixed with 30 ml of hydrazine. After 3 days of stirring in an open flask at 20° C., it is concentrated by evaporation in a vacuum, the residue suspended in water, suctioned off, dried in a vacuum and recrystallized from pyridine/ether.

Yield: 1.96 g (93% of theory) of reddish brown powder
Analysis (relative to the anhydrous substance): C 68.19 H 5.97 N 13.83 Zn 8.07 O 3.95 Cld. C 67.86 H 5.83 N 13.61 Zn 7.94 c) Manganese(III)-[3,8-bis-(2-phenylethyl)-deuteroporphyrin-IX-dihydrazide]-acetate 1.90 g (2.34 mmol) of the compound produced in example 17b is refluxed with 9.50 g of manganese(II)acetate for 1 hour in 500 ml of acetic acid. Then, it is concentrated by evaporation in a vacuum, the residue is suspended in water, filtered off and washed with water. The dried crude product is recrystallized from dimethylformamide.

Yield: 1.65 g (82% of theory) of reddish brown powder
Analysis (relative to the anhydrous substance): C 67.12 H 5.98 Mn 6.40 N 13.05 O 7.45 Cld. C 66.93 H 5.91 Mn 6.32 N 12.89 d) Manganese(III)-{N,N'-bis-[11-carboxy-2-oxo-4,7-bis-(carboxymethyl)-10-(ethoxycarbonylmethyl)-1,4,7,10-tetraazaundecyl]-3,8-bis-(2-phenylethyl)-deuteroporphyrin-IX-13,17-diamide}-acetate 1.41 g (3.49 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 250 ml of anhydrous dimethylformamide. It is covered with nitrogen, 1.77 g (17.50 mmol) of triethylamine and 1.50 g (1.75 mmol) of the compound produced in example 17c are added and stirred for 3 days at room temperature. After filtering and concentration by evaporation in a vacuum, the residue is chromatographed on silica gel RP-18 with water/tetrahydrofuran and the eluate is evaporated to dryness in a vacuum.

Yield: 2.10 g (72% of theory) of reddish brown powder
Analysis (relative to the anhydrous substance): C 57.69 H 6.11 N 11.77 Mn 3.30 O 21.13 Cld. C 57.42 H 5.99 N 11.61 Mn 3.24 e) Manganese(III)-{N,N'-bis-[11-carboxylato-2-oxo-4,7,10-tris-(carboxylatomethyl)-1,4,7,10-tetraazaundecyl]-3,8-bis-(2-phenylethyl)-deuteroporphyrin-IX-13,17-diamide}-acetate, digadolinium complex, disodium salt 2.00 g (1.20 mmol) of the ligand produced in example 17cl is suspended in 400 ml of water. After addition of 10 molar aqueous sodium hydroxide solution, it is adjusted to pH 13 and stirred for 5 hours at room temperature. After completion of the saponification of the ester, it is adjusted to pH 7.0, 1.06 g (2.64 mmol) of gadolinium acetate tetrahydrate is added and by addition of 2 n sodium hydroxide solution, the pH is held at 7.0. After stirring overnight, it is filtered, the solvent is removed in a vacuum, the residue is chromatographed on silica gel RP-18 with water/tetrahydrofuran and the eluate is evaporated to dryness in a vacuum.

Yield: 1.62 g (69% of theory) of reddish brown powder
Analysis (relative to the anhydrous substance):
C 46.53 H 4.37 N 10.00 Gd 16.03 Mn 2.80 Na 2.33 O 17.94 Cld. C 46.33 H 4.28 N 9.86 Gd 17.86 Mn 2.67 Na 2.41

EXAMPLE 18 a) Zinc(II)-[3,8-bis-(2-(naphth-1-yl)-ethenyl)-deuteroporphyrin-IX-dimethyl ester]

3.23 g (6.69 mmol) of naphth-1-yl-methyl-triphenylphosphoniumbromide in 600 ml of anhydrous tetrahydrofuran is mixed under argon at room temperature with a solution of 0.43 g (6.69 mmol) of butyllithium. After completion of the reaction to the ylide, 2.00 g (3.04 mmol) of Zn-[3,8-diformyl-deuteroporphyrin-IX-dimethyl ester] (Kevin M. Smith, Eugene M. Fujinari, Kevin C. Langry, Daniel W. Parish and Hani D. Tabba, J. Am. Chem. Soc. 105, 6638–6646 (1983)) is added and stirred for two more hours. After addition of 30 ml of methanol, the solvent is substantially removed in a vacuum and the residue shaken out with methylene chloride and semiconcentrated aqueous sodium bicarbonate solution. The organic phase is dried on sodium sulfate, concentrated by evaporation and chromatographed on aluminum oxide (Merck, activity stages 2–3) with methylene chloride/methanol and the eluate is evaporated to dryness.

Yield: 2.53 g (92%) of reddish brown powder
Analysis (relative to the anhydrous substance): C 74.21 H 5.34 N 6.18 Zn 7.21 O 7.06 Cld. C 74.00 H 5.19 N 5.99 Zn 7.11 b) Zinc(II)-[3,8-bis-(2-(naphth-1-yl)-ethyl)-deuteroporphyrin-IX-dihydrazide]

2.50 g (2.76 mmol) of the compound produced in example 18a is dissolved in 130 ml of pyridine and mixed with 30 ml of hydrazine. After 3 days of stirring at room temperature in an open flask at 20° C., it is concentrated by evaporation in a vacuum, the residue suspended in water, suctioned off, dried in a vacuum and recrystallized from pyridine/ether.

Yield: 2.39 g (95% of theory) of reddish brown powder
Analysis (relative to the anhydrous substance): C 71.24 H 5.76 N 12.31 Zn 7.18 O 3.51 Cld. C 70.93 H 5.59 N 12.01 Zn 7.09 c) Zinc(II)-{N,N'-bis[11-carboxy-2-oxo-4,7-bis-(carboxymethyl)-10-(ethoxycarbonylmethyl)-1,4,7,10-tetraazaundecyl]-3,8-bis-(2-(naphth-1-yl)-ethyl)-deuteroporphyrin-IX-13,17-diamide}

1.77 g (4.40 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 300 ml of anhydrous dimethylformamide. It is covered with nitrogen, 2.20 g (21.75 mmol) of triethylamine and 2.00 g (2.20 mmol) of the compound produced in example 18b are added and stirred for 3 days at room temperature. After filtering and concentration by evaporation in a vacuum, the residue is chromatographed on silica gel RP-18 with water/tetrahydrofuran. The eluate is evaporated to dryness in a vacuum.

Yield: 2.91 g (77% of theory) of reddish brown powder
Analysis (relative to the anhydrous substance): C 60.15 H 5.99 N 11.42 Zn 3.81 O 18.63 Cld. C 59.89 H 5.81 N 11.26 Zn 3.72 d) Zinc(II)-{N,N'-bis[11-carboxylato-2-oxo-4,7,10-tris-(carboxylatomethyl)-1,4,7,10-tetraazaundecyl]-3,8-bis-(2-(naphth-1-yl)-ethyl)-deuteroporphyrin-IX-13,17-diamide}, digadolinium complex, disodium salt 2.00 g (1.16 mmol) of the ligand produced in example 18c is suspended in 400 ml of water. After addition of 10 molar aqueous sodium hydroxide solution, it is adjusted to pH 13 and stirred for 5 hours at room temperature. After completion of the saponification of the ester, it is adjusted to pH 7.0, 1.06 g (2.64 mmol) of gadolinium acetate tetrahydrate is added and by addition of 2 n sodium hydroxide solution, the pH is held at 7.0. After stirring overnight, it is filtered, the solvent is removed in a vacuum, the residue is chromatographed on silica gel RP-18 with water/tetrahydrofuran and the eluate is evaporated to dryness in a vacuum.

Yield: 1.47 g (63% of theory) of reddish brown powder
Analysis (relative to the anhydrous substance): C 48.92 H 4.31 N 9.74 Na 2.27 Gd 15.62 Zn 3.25 O 15.89 Cld. C 48.66 H 4.21 N 9.48 Na 2.31 Gd 15.46 Zn 3.18

EXAMPLE 19 a) 13,17-Bis-(4-aminobutyl)-3,8-diethyl-2,7,12,18-tetramethylporphyrin 2.00 g (3.59 mmol) of 13,17-bis-(3-cyanopropyl)-3,8-diethyl-2,7,12,18-tetramethylporphyrin is added in portions to the reducing agent formed from 0.32 g (14.5 mmol) of lithium borohydride and 3.18 g (29.0 mmol) of trimethyl-silyl chloride (A. Giannis, K. Sandhoff, Angewandte Chemie [Applied Chemistry]101 No. 2, 220–222 (1989)) in 100 ml of anhydrous tetrahydrofuran and stirred for 24 hours under argon at 25° C. If by thin-layer chromatography more feedstock is detectable, a further reducing agent is added and stirred again. For working-up, 20 ml of methanol is carefully instilled, it is adjusted to pH 1.0 with semiconcentrated hydrochloric acid and allowed to stir for one hour. The batch is then adjusted strongly alkaline by addition of 20 ml of 30% sodium hydroxide solution, stirred for 30 minutes and shaken out twice with methylene chloride. The organic phases are combined, dried on anhydrous sodium sulfate, filtered and concentrated by evaporation. The reddish brown, solid residue is reused as crude product.

Yield: 1.80 g (89% of theory) of reddish brown solid b) 13,17-Bis-[4-N-(benzyloxycarbonyl)-aminobutyl]-3,8-diethyl-2,7,12,18-tetramethyl-porphyrin 50 mg (0.09 mmol) of the compound produced in example 19a is dissolved in 5 ml of anhydrous pyridine. 34 mg (0.20 mmol) of benzyloxycarbonyl chloride is instilled in the solution stirred at —10° C. under argon and the batch is allowed to stir for 12 more hours at room temperature. Then, the solvent is removed, taken up in methylene chloride, and shaken out once with 2 n citric acid solution and once with concentrated sodium bicarbonate solution and the organic phase is dried on sodium sulfate. It is filtered, concentrated by evaporation, chromatographed on aluminum oxide with methylene chloride/methanol and evaporated to dryness.

Yield: 61 mg (81% of theory) of reddish brown solid
Analysis (relative to the anhydrous substance): C 74.97 H 7.26 N 10.09 O 7.68 Cld. C 74.76 H 7.19 N 9.88 c) 13,17-Bis-[15-carboxy-6-oxo-8,11-bis-(carboxymethyl)-14-(ethoxycarbonylmethyl)-5,8,11,14-tetraazapentadecyl]-3,8-diethyl-2,7,12,18-tetramethylporphyrin 1.21 g (3.00 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 200 ml of anhydrous dimethylformamide. It is covered with nitrogen, 1.52 g (15.00 mmol) of triethylamine and 0.85 g (1.50 mmol) of the compound produced in example 19a are added and stirred for 3 days at room temperature. After filtering and concentration by evaporation in a vacuum, the residue is chromatographed on silica gel RP-18 with water/tetrahydrofuran and the eluate is concentrated by evaporation in a vacuum.

Yield: 1.50 g (73% of theory) of reddish brown powder
Analysis (relative to the anhydrous substance): C 59.55 H 7.20 N 12.25 O 21.00 Cld. C 59.41 H 7.14 N 12.13 d) 13,17-Bis-[15-carboxylato-6-oxo-8,11-bis-(carboxylatomethyl)-14-(ethoxycarbonylmethyl)-5,8,11,14-tetraazapentadecyl]-3,8-diethyl-2,7,12,18-tetramethylporphyrin, digadolinium complex 1.20 g (0.87 mmol) of the ligand produced in example 19c is dissolved in 400 ml of water. After addition of 2 n aqueous sodium hydroxide solution, it is adjusted to pH 7.0 and 0.78 g (1.91 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 with water/tetrahydrofuran and the eluate is evaporated to dryness in a vacuum.

Yield: 1.01 g (69% of theory) of reddish brown powder
Analysis (relative to the anhydrous substance): C 48.62 H 5.52 Gd 18.72 N 10.10 O 17.14 Cld. C 48.46 H 5.47 Gd 18.75 N 9.83 e) 13,17-Bis-(15-carboxylato-6-oxo-8,11,14-tris-(carboxylatomethyl)-5,8,11,14-tetraazapentadecyl]-3,8-diethyl-2,7,12,18-tetramethylporphyrin, digadolinium complex, disodium salt 0.90 g (0.66 mmol) of the ligand produced in example 19c is dissolved in 300 ml of water. After addition of 10 molar aqueous sodium hydroxide solution, it is adjusted to pH 13.0 and it is stirred for 5 hours at room temperature. After completion of the saponification of the ester, it is adjusted to pH 7.0 with concentrated hydrochloric acid, and as described in example 19d, complexed and purified with 0.59 g (1.44 mmol) of gadolinium acetate tetrahydrate.

Yield: 0.91 g (83% of theory) of reddish brown powder
Analysis (relative to the anhydrous substance): C 46.09 H 4.96 Gd 18.86 N 10.08 Na 2.75 O 17.27 Cld. C 45.85 H 4.87 Gd 18.72 N 9.84 Na 2.54

EXAMPLE 20 a) 13,17-Bis-[4-(4-aminophenyl)-4-oxabutyl]-3,8-diethyl-2,7,12,18-tetramethylporphyrin 3.28 g (30.10 mmol) of 4-aminophenol and 1.69 g (30.10 mmol) of powdered potassium hydroxide are stirred in 50 ml of anhydrous dimethylformamide under argon for 30 minutes at room temperature and then mixed with 2.00 g (3.01 mmol) of 13,17-bis-(3-bromopropyl)-3,8-diethyl-2,7,12,18-tetramethylporphyrin (CA RN 112635–99–1). After 30 hours of stirring at room temperature, it is filtered, substantially concentrated by evaporation in a vacuum, the residue is taken up in methylene chloride and shaken out once each with water and with saturated aqueous sodium bicarbonate solution. The organic phase is dried on sodium sulfate, filtered and concentrated by evaporation and the residue is chromatographed to aluminum oxide with methylene chloride/methanol. After the concentration by evaporation, the product is obtained as reddish brown solid, which can be recrystallized from methylene chloride/ether.

Yield: 1.97 g (91% of theory) of reddish brown powder
Analysis (relative to the anhydrous substance): C 76.64 H 7.27 N 11.66 O 4.44 Cld. C 76.48 H 7.21 N 11.54 b) 13,17-Bis-{4-(4-(11-carboxy-2-oxo-4,7-bis-(carboxymethyl)-10-(ethoxycarbonylmethyl)-1,4,7,10-tetraazaundecyl)-phenyl]-4-oxabutyl}-3,8-diethyl-2,7,12,18-tetramethylporphyrin 1.21 g (3.00 mmol) of 3-ethoxy-carbonylmethyl-6-[2-(2,6-dioxomorpholino)-ethyl]-3,6-diazaoctanedioic acid (DTPA-monoanhydridemonoethyl ester) is suspended in 200 ml of anhydrous dimethylformamide. It is covered with nitrogen, 1.52 g (15.00 mmol) of triethylamine and 1.08 g (1.50 mmol) of the compound produced in example 20a are added and stirred for 3 days at room temperature. After filtering and concentration by evaporation in a vacuum, the residue is chromatographed on silica gel RP-18 with water/tetrahydrofuran and evaporated to dryness in a vacuum.

Yield: 1.89 g (82% of theory) of reddish brown powder
Analysis (relative to the anhydrous substance): C 61.32 H 6.73 N 11.00 O 20.95 Cld. C 61.09 H 6.64 N 10.87 c) 13,17-Bis-{4-(4-(11-carboxylato-2-oxo-4,7-bis-(carboxylatomethyl)-10-(ethoxycarbonylmethyl)-1,4,7,10-tetraazaundecyl)-phenyl]-4-oxabutyl}-3,8-diethyl-2,7,12,18-tetramethylporphyrin, digadolinium complex 1.50 g (0.98 mmol) of the ligand produced in example 20b is dissolved in 350 ml of water. After addition of 2 n aqueous sodium hydroxide solution, it is adjusted to pH 7.0 and 0.88 g (2.16 mmol) of gadolinium acetate tetrahydrate and 2 n aqueous sodium hydroxide solution are added in portions, so that the pH of the reaction mixture always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 with water/tetrahydrofuran. The eluate is evaporated to dryness in a vacuum.

Yield: 1.44 g (80% of theory) of reddish brown powder
Analysis (relative to the anhydrous substance): C 51.02 H 5.27 Gd 17.13 N 9.15 O 17.43 Cld. C 50.83 H 5.18 Gd 17.11 N 8.94 d) 13,17-Bis-{4-(4-(11-carboxylato-2-oxo-4,7,10-tris-(carboxylatomethyl)-1,4,7,10-tetraazaundecyl)-phenyl]-4-oxabutyl}-3,8-diethyl-2,7,12,18-tetramethylporphyrin, digadolinium complex, disodium salt 1.50 g (0.98 mmol) of the ligand produced in example 20b is dissolved in 350 ml of water. After addition of 10 molar aqueous sodium hydroxide solution, it is adjusted to pH 13.0 and stirred for 5 hours at room temperature. After completion of the saponification of the ester, it is adjusted to pH 7.0 with concentrated hydrochloric acid, and as described in example 20c, complexed, worked up and purified with 0.88 g (2.16 mmol) of gadolinium acetate tetrahydrate.

Yield: 1.41 g (79% of theory) of reddish brown powder

Analysis (relative to the anhydrous substance): C 48.73 H 4.75 Gd 17.24 N 9.22 Na 2.51 O 17.54 Cld. C 48.61 H 4.72 Gd 17.25 N 9.13 Na 2.39

EXAMPLE 21 a) Manganese(III)-{N,N'-bis-[11-carboxy-2-oxo-4,7-bis-(carboxymethyl)-10-(ethoxycarbonylmethyl)-1,4,7,10-tetraazaundecyl]-3,8-bis-(1-propyl)-deuteroporphyrin-IX-13,17-diamide}-acetate 2.00 g (1.40 mmol) of the ligand produced in example 14d and 10.00 g of manganese(II)acetate tetrahydrate were refluxed in 150 ml of acetic acid for one hour. The above is evaporated to dryness in a vacuum and the residue is chromatographed in a mixture of dichloromethane, methanol, acetic acid and water. The product-containing fractions yield a finely crystalline, reddish brown powder after concentration by evaporation and drying in a vacuum.

Yield: 2.01 g (93% of theory)

Analysis (relative to the anhydrous substance): C 54.54 H 6.34 Mn 3.56 N 12.72 O 22.83 Cld. C 54.63 H 6.41 Mn 3.42 N 12.58 b) Manganese(III)-{N,N'-bis-[11-carboxylato-2-oxo-4,7-bis-(carboxylatomethyl)-10-(ethoxycarbonylmethyl)-1,4,7,10-tetraazaundecyl]-3,8-bis-(1-propyl)-deuteroporphyrin-IX-13,17-diamide}-acetate, digadolinium complex 1.92 g (1.25 mmol) of the ligand produced in example 21a is dissolved in 300 ml of water. After addition of 2 n sodium hydroxide solution, it is adjusted to pH 7.0 and 1.18 g (2.90 mmol) of gadolinium acetate tetrahydrate and 2 n aqueous sodium hydroxide solution are added in portions, so that the pH always fluctuates between 6.8 and 7.2. After all gadolinium acetate has been added, it is stirred overnight at room temperature. For working-up, it is filtered, the solvent is removed in a vacuum and the residue is chromatographed on silica gel RP-18 with water/tetrahydrofuran. The fractions contained in the product are evaporated to dryness in a vacuum.

Yield: 1.89 g (82% of theory) of reddish brown powder

Analysis (relative to the anhydrous substance): C 45.45 H 4.96 Gd 17.00 Mn 2.97 N 10.60 O 19.03 Cld. C 45.22 H 4.83 Gd 16.89 Mn 3.05 N 10.50 c) Manganese(III)-{N,N'-bis-[11-carboxylato-2-oxo-4,7-bis-(carboxylatomethyl)-10-(ethoxycarbonylmethyl)-1,4,7,10-tetraazaundecyl]-3,8-bis-(1-propyl)-deuteroporphyrin-IX-13,17-diamide}-acetate, digadolinium complex, disodium salt 1.55 g (1.01 mmol) of the manganese porphyrin produced in example 21a is dissolved in 150 ml of water. After addition of 10 molar aqueous sodium hydroxide solution, it is adjusted to pH 13.0 and stirred for 5 hours at room temperature. After completion of the saponification of the ester, it is adjusted to pH 7.0 with concentrated hydrochloric acid, and as described in example 21b, complexed and purified with 0.90 g (2.21 mmol) of gadolinium acetate tetrahydrate.

Yield: 1.45 g (78% of theory) of reddish brown powder

Analysis (relative to the anhydrous substance): C 43.13 H 4.44 Gd 17.11 Mn 2.99 N 10.67 Na 2.50 O 19.5 Cld. C 43.24 H 4.52 Gd 17.03 Mn 2.84 N 10.39 Na 2.81

EXAMPLE 22 a) 9 nude mice (Balb/c nu/nu) with subcutaneously implanted colon cancers (HT29, WiDr) were each administered by i.v. 0.1 mmol/kg of the mesoporphyrin derivative of example 1b (10 mmol/l dissolved in bidistilled water, pH 7.2, 37° C.). After 0.5, 3 and 24 hours the animals were killed and dissected. The tissue concentrations were determined after corresponding working-up ($HNO_3$ conc.) by ICP-AES and calculated for % of the administered dose per gram of tissue net weight.

TABLE 1

| | % of dose/g organ | | |
|---|---|---|---|
| | over 0.5 hour MW ± S | over 3 hours MW ± S | over 24 hours MW ± S |
| blood | 19.34 ± 1.06 | 6.11 ± 1.13 | 0.21 ± 0.04 |
| liver | 9.26 ± 0.10 | 8.68 ± 0.53 | 10.47 ± 0.64 |
| kidneys | 42.29 ± 7.05 | 6.71 ± 0.79 | 3.93 ± 1.01 |
| spleen | 7.02 ± 0.53 | 3.21 ± 0.46 | 3.85 ± 0.63 |
| muscle | 3.13 ± 0.68 | 0.85 ± 0.15 | 0.53 ± 0.04 |
| intestine | 3.53 ± 0.07 | 2.03 ± 0.13 | 0.95 ± 0.30 |
| skin | 8.63 ± 0.91 | 2.81 ± 0.30 | 2.71 ± 0.42 |
| lung | 13.83 ± 1.43 | 4.57 ± 0.67 | 1.84 ± 0.38 |
| HT29 tumor | 4.80 ± 1.23 | 3.03 ± 0.22 | 1.95 ± 0.52 |
| WiDr tumor | 4.54 ± 3.37 | 3.23 ± 0.95 | 2.71 ± 0.57 |
| rest of body | 4.84 ± 0.48 | 1.57 ± 0.21 | 1.20 ± 0.45 |

By 0.5 hour p.i., the concentration in the liver is already 10% of the administered dose per gram of tissue net weight. While in all other tissues examined, the concentration drastically decreases within 24 hours, the porphyrin concentration in the liver tissue remains constant at 10%.

TABLE 2

| | Average values (enhancement): | | | | |
|---|---|---|---|---|---|
| Time (min) | HT29 | WiDr | Liver | Kidneys | Muscle |
| 0 | 1.00 | 1.00 | 1.00 | 1.00 | 1.00 |
| 5 | 1.36 | 1.16 | 1.43 | 2.89 | 1.41 |
| 15 | 1.49 | 1.16 | 1.43 | 2.70 | 1.41 |
| 30 | 1.54 | 1.18 | 1.40 | 2.65 | 1.39 |
| 45 | 1.55 | 1.25 | 1.42 | 2.79 | 1.40 |
| 60 | 1.59 | 1.05 | 1.38 | 2.56 | 1.29 |
| 75 | 1.97 | 1.23 | 1.51 | 2.53 | 1.47 |
| 90 | 1.51 | 1.28 | 1.43 | 2.40 | 1.50 |
| 120 | 1.64 | 1.22 | 1.47 | 2.15 | 1.34 |
| 24 hours | 1.05 | 1.64 | 1.19 | 1.51 | 1.24 |

Already 5 minutes p.i., a marked signal intensity increase on the liver tissue was detected and after 30 minutes in the tumor examined. The maximum enhancement (liver: +50%, tumor: +100%) was achieved in 75 minutes p.i. On the other hand, only a small change was noted in the muscle as reference tissue. A stronger signal intensity change was noted in the kidneys.

EXAMPLE 23

On a Bruker Biospec nuclear spin tomograph (2.35 Tesla), the al intensity change in various tissues of tumor-bearing (HT29 colon cancer) nude mice (Balb/c nu/nu) was studied after i.v administration of 0.05 mmol/kg of the compound according to example 1c (10 mmol/l, pH 7.2; 37° C. in bidistilled water). The measurement takes place with a multi slice single echo sequence (MSSE). Imaging parameters: TR: 400 ms, TE: 30 ms, layer thickness: 4 mm, number of averages: 4/slice, matrix $256^2$. After a preliminary image, 0.05 mmol/kg of the substance was administered and the signal intensity change (relative to an internal standard) was studied 5, 15, 30, 45, 60, 75, 90 and 120 minutes p.i.

TABLE 3

| | Enhancement after intravenous administration of 0.05 mmol/kg of body weight | | | |
|---|---|---|---|---|
| Time (min) | liver | muscle | HT29 | Kidneys |
| 0 | 100 | 100 | 100 | 100 |
| 5 | 122 ± 31 | 119 ± 8 | 116 ± 19 | 185 ± 34 |
| 60 | 164 ± 22 | 129 ± 7 | 128 ± 21 | 240 ± 26 |
| 90 | 202 ± 37 | 143 ± 21 | 148 ± 22 | 248 ± 18 |
| 120 | 194 ± 33 | 147 ± 17 | 155 ± 30 | 246 ± 6 |
| 150 | 197 ± 17 | 146 ± 8 | 167 ± 29 | 225 ± 12 |
| 180 | 212 ± 9 | 157 ± 8 | 161 ± 22 | 212 ± 16 |

A marked signal intensity increase in the liver tissue occurred as early as 5 minutes p.i., while only a slight change was able to be noted in tumor and muscle as reference tissues. This effect lasted during the entire observation time. Only in the kidneys is it possible to note an even stronger signal intensity change up to 3 hours p.i.

b) On a Bruker Biospec nuclear spin tomograph (2.35 Tesla), the signal intensity change in various tissues of rats with a DMBA-induced breast cancer was studied after i.v. administration of 0.05 mmol/kg or 0.1 mmol of the compound of example 1c (20 mmol/l, pH 7.2; 37° C. in bidistilled water). The measurements took place with a multi slice variable echo sequence (MSVE). Imaging parameters: TR: 400 ms, TE: 25 ms, layer thickness: 4 mm, number of averages: 4/slice, matrix $256^2$.

After a preliminary image, 0.05 mmol/kg or 0.1 mmol/kg of the substance was administered and the signal intensity change (relative to an internal standard) was studied.

The results are compiled in the table below. The $^1$H-NMR images of the DMBA-induced breast cancer after administration of 0.1 mmol/kg i.v. after 5 minutes or 3 or 24 hours p.i. are reproduced in FIG. 1.

TABLE 4

| | Enhancement after intravenous administration of 0.05 mmol/kg (average values) | | | |
|---|---|---|---|---|
| Time(min) | Tumor | Liver | Kidneys | Muscle |
| 0 | 1.00 | 1.00 | 1.00 | 1.00 |
| 5 | 1.88 | 1.48 | 2.57 | 1.34 |
| 15 | 1.97 | 1.29 | 2.81 | 1.26 |
| 30 | 1.71 | 1.42 | 2.94 | 1.22 |
| 45 | 1.71 | 1.49 | 2.84 | 1.12 |
| 60 | 1.50 | 1.52 | 2.53 | 1.10 |
| 75 | 1.71 | 1.50 | 2.47 | 1.04 |
| 90 | 1.62 | 1.53 | 2.15 | 1.11 |
| 105 | 1.75 | 1.63 | 2.63 | 1.07 |
| 160 | 1.69 | 1.47 | 2.38 | 1.07 |
| 180 | 1.67 | 1.57 | 2.54 | 1.02 |
| 24 hours | 1.31 | 0.93 | 1.17 | 1.07 |

TABLE 5

| | Enhancement after intravenous administration of 0.1 mmol/kg (average values) | | | |
|---|---|---|---|---|
| Time(min) | Tumor | Liver | Kidneys | Muscle |
| 0 | 1.00 | 1.00 | 1.00 | 1.00 |
| 1 | 2.48 | 1.55 | 1.16 | 1.46 |
| 15 | 2.40 | 1.61 | 2.36 | 1.30 |
| 26 | 2.41 | 1.45 | 2.33 | 1.37 |
| 40 | 2.34 | 1.51 | 2.38 | 1.23 |

TABLE 5-continued

| | Enhancement after intravenous administration of 0.1 mmol/kg (average values) | | | |
|---|---|---|---|---|
| Time(min) | Tumor | Liver | Kidneys | Muscle |
| 60 | 2.34 | 1.36 | 1.86 | 1.23 |
| 71 | 2.36 | 1.62 | 1.66 | 1.17 |
| 85 | 2.39 | 1.48 | 1.64 | 1.32 |
| 115 | 2.38 | 1.62 | 2.43 | 1.23 |
| 150 | 2.31 | 1.48 | 2.27 | 1.17 |
| 180 | 2.38 | 1.59 | 2.18 | 1.22 |
| 24 hours | 2.02 | 1.33 | 0.94 | 1.15 |

As early as 5 minutes p.i., a marked signal intensity increase in the liver tissue and especially in the studied tumors occurred. On the other hand, only a slight change was noted in muscle as reference tissue. This effect lasted during the entire observation time (up to 24 hours p.i.). Only in the kidneys is it possible to note a stronger signal intensity change after administration of 0.05 mmol/kg.

c) On a Bruker Biospec nuclear spin tomograph (2.35 Tesla), the signal intensity change in various tissues of tumor-bearing (Novikoff-hepatoma, i.m.) nude rats (LEW/Mol rnu/rnu) was studied after a one-time intravenous administration of 0.1 mmol/kg of the compound of example 1c (20 mmol/l; pH 7.2–7.4; 37° C. in tris/NaCl buffer). The measurements were made with a multi slice single echo sequence (MSSE). Imaging parameters: TR: 412 ms, TE: 25 ms, layer thickness: 4 mm, number of averages: 4/slice, matrix $256^2$. After a preliminary image, 0.1 mmol/kg each of the substance was administered in a caudal vein and the signal intensity changes (relative to an also measured standard) were studied at intervals of 15 or 30 minutes up to 180 minutes p.i. The relative intensities relative to the respective initial intensity (=1.00 set) are indicated.

TABLE 6

| | Average enhancement n = 3: | | | |
|---|---|---|---|---|
| Time(min) | Tumor MW ± S | Liver MW ± S | Kidneys MW ± S | Muscle MW ± S |
| 0 | 1.00 ± 0.00 | 1.00 ± 0.00 | 1.00 ± 0.00 | 1.00 ± 0.00 |
| 1 | 1.63 ± 0.24 | 1.43 ± 0.24 | 1.67 ± 0.35 | 1.60 ± 0.01 |
| 15 | 1.71 ± 0.19 | 1.34 ± 0.22 | 2.13 ± 0.28 | 1.54 ± 0.06 |
| 30 | 1.72 ± 0.23 | 1.31 ± 0.21 | 2.14 ± 0.38 | 1.47 ± 0.08 |
| 45 | 1.79 ± 0.21 | 1.17 ± 0.16 | 2.10 ± 0.30 | 1.41 ± 0.10 |
| 60 | 1.78 ± 0.24 | 1.31 ± 0.09 | 2.12 ± 0.19 | 1.33 ± 0.05 |
| 75 | 1.64 ± 0.17 | 1.37 ± 0.05 | 1.93 ± 0.19 | 1.37 ± 0.01 |
| 90 | 1.75 ± 0.27 | 1.22 ± 0.24 | 1.96 ± 0.08 | 1.24 ± 0.03 |
| 120 | 1.77 ± 0.23 | 1.23 ± 0.07 | 1.92 ± 0.33 | 1.28 ± 0.08 |
| 150 | 1.73 ± 0.23 | 1.16 ± 0.22 | 1.86 ± 0.18 | 1.20 ± 0.06 |
| 180 | 1.85 ± 0.09 | 1.07 ± 0.20 | 1.84 ± 0.24 | 1.15 ± 0.04 |
| 190 | 1.45 ± 0.00 | 1.27 ± 0.00 | 1.73 ± 0.00 | 1.21 ± 0.00 |

Directly after administration, a marked increase in the al intensity (±60%) occurred in the studied tissues. But while in liver and muscles the initial intensity almost returned after 2–3 hours, the intensity in the tumor remained at an almost unchanged high level during the observation time. The substance is obviously eliminated mainly renally. Therefore, the signal intensity in the kidneys was high above that which could be determined in the tumors for up to 150 minutes.

d) On a Bruker Biospec nuclear spin tomograph (2.35 Tesla), the signal intensity change in various tissues of tumor-bearing (HT29 and WiDr colon cancer) nude mice (Balb/c nu/nu) was studied after i.v. administration of 0.5 mmol/kg of the compound of example 1c (10 mmol/l, pH 7.2; 37° C. in bidistilled water). The measurement takes place with a multi slice single echo sequence (MSSE). Imaging parameters: TR: 400 ms, TE: 30 ms, layer thickness: 4 mm, number of averages: 4/slice, matrix $256^2$. After a preliminary image, 0.5 mmol/kg of the substance was administered and the signal intensity change studied up to 180 minutes p.i.

As early as 5 minutes p.i., a marked signal intensity increase occurred in the liver tissue and in both studied tumors. However, a smaller signal increase could be noted in the muscle as reference tissue. This effect lasted during the entire observation time. FIG. 2 shows the $^1$H-NMR image of the WiDr colon cancer after 5, 82 or 180 minutes p.i., FIG. 3 that of the HT29 carcinoma.

e) 9 nude mice (Balb/c nu/nu) with subcutaneously implanted colon cancers (HT29 and WiDr) were each administered by i.v. 0.1 mmol/kg of the deuteroporphyrin derivative of the compound according to example 1c (10 mmol/l dissolved in bidistilled water, pH 7.2, 37° C.). After 0.5, 3 and 24 hours, the animals were killed and dissected. The tissue concentrations were determined after corresponding working-up ($HNO_3$ conc.) by ICP-AES and calculated for % of the administered dose per gram of tissue net weight. Moreover, tissue relaxation times T1 and T2 were determined (Bruker minispec pc 120).

TABLE 7

% of the administered dose per gram of tissue net weight

|  | 0.5 hour | 3 hours | 24 hours |
| --- | --- | --- | --- |
| blood | 4.78 ± 0.77 | 2.60 ± 0.91 | 0.13 ± 0.15 |
| liver | 1.87 ± 0.71 | 2.03 ± 0.34 | 2.05 ± 0.00 |
| kidneys | 4.06 ± 1.01 | 4.47 ± 1.63 | 4.20 ± 0.27 |
| spleen | 1.31 ± 1.20 | 0.62 ± 0.19 | 0.63 ± 0.06 |
| muscle | 0.38 ± 0.14 | 0.35 ± 0.02 | 0.10 ± 0.02 |
| intestine | 0.32 ± 0.09 | 0.49 ± 0.07 | 1.56 ± 0.65 |
| skin | 2.80 ± 0.71 | 1.61 ± 0.14 | 0.65 ± 0.12 |
| lung | 2.45 ± 0.14 | 1.71 ± 0.37 | 0.16 ± 0.03 |
| HT29 tumor | 1.09 ± 0.14 | 1.46 ± 0.22 | 0.86 ± 0.14 |
| WiDr tumor | 1.51 ± 0.20 | 1.25 ± 0.16 | 0.58 ± 0.02 |
| rest of body | 1.13 ± 0.04 | 0.58 ± 0.07 | 0.26 ± 0.04 |

Because of the high relaxivity of the compound (17.86 1 $mmol^{-1}s^{-1}$), markedly shortened T1-tissue relaxation times were able to be measured (factor 2–3) despite the relatively small tissue concentrations in both tumors. This shortening of the relaxation times should be sufficient at least up to 3 hours p.i. for an enhancement in the NMR imaging experiment (T1-weighted spin echo sequence).

TABLE 8

Tissue relaxation time $T_1$

| $T_1$ (ms) | 0.5 hour | 3 hours | 24 hours | Control |
| --- | --- | --- | --- | --- |
| liver | 220 ± 20 | 220 ± 30 | 260 ± 10 | 380 ± 30 |
| kidneys | 160 ± 10 | 230 ± 30 | 240 ± 20 | 500 ± 20 |
| muscle | 500 ± 40 | 560 ± 40 | 660 ± 10 | 580 ± 10 |
| HT29 tumor | 410 ± 30 | 440 ± 70 | 540 ± 20 | 840 ± 50 |
| WiDr tumor | 320 ± 40 | 430 ± 50 | 640 ± 10 | 760 ± 100 |

TABLE 9

Tissue relaxation time $T_2$

| $T_2$ (ms) | 0.5 hour | 3 hours | 24 hours | Control |
| --- | --- | --- | --- | --- |
| liver | 34 ± 3 | 42 ± 2 | 48 ± 7 | 51 ± 2 |
| kidneys | 42 ± 1 | 47 ± 5 | 54 ± 10 | 69 ± 4 |
| muscle | 32 ± 1 | 36 ± 3 | 31 ± 1 | 58 ± 5 |
| HT29 tumor | 81 ± 4 | 72 ± 8 | 83 ± 7 | 101 ± 8 |
| WiDr tumor | 67 ± 7 | 72 ± 7 | 85 ± 2 | 118 ± 19 | f) 9 nude mice (Balb/c nu/nu) with subcutaneously implanted carcinomas (HT29, WiDr and MATLu) were each administered by i.v. 0.1 mmol/kg of the deuteroporphyrin derivative of example 1c (10 mmol/L dissolved in bidistilled water, pH 7.2, 37° C.). After 2 hours, the animals were killed and dissected. The tissue concentrations were determined after corresponding working-up ($HNO_3$ conc.) by ICP-AES and calculated for % of the administered dose per gram of tissue net weight. Moreover, tissue relaxation times T1 and T2 were determined (Bruker minispec pc 120). To determine the blank readings, control animals were correspondingly studied without KM-administration.

TABLE 10

% of the administered dose per gram of tissue net weight

|  | HT29 | WiDr | MATLu |
| --- | --- | --- | --- |
| blood | 2.74 ± 0.90 | 2.13 ± 0.01 | 1.14 ± 0.10 |
| liver | 1.49 ± 0.17 | 1.28 ± 0.07 | 0.97 ± 0.11 |
| kidneys | 6.23 ± 1.80 | 4.23 ± 0.19 | 2.73 ± 0.33 |
| spleen | 0.64 ± 0.21 | 0.44 ± 0.04 | 0.31 ± 0.06 |
| muscle | 0.24 ± 0.11 | 0.19 ± 0.03 | 0.26 ± 0.10 |
| intestine | 1.18 ± 0.22 | 0.73 ± 0.34 | 0.68 ± 0.08 |
| skin | 1.34 ± 0.52 | 0.87 ± 0.13 | 0.41 ± 0.38 |
| lung | 2.09 ± 0.42 | 1.54 ± 0.09 | 3.69 ± 3.58 |
| HT29 | 1.00 ± 0.27 |  |  |
| WiDr |  | 0.83 ± 0.05 |  |
| MATLu |  |  | 1.92 ± 2.09 |
| rest of body | 0.54± | 0.4 ± 0.04 | 0.27 ± 0.01 |

In all three tumors, i.a. because of the high relaxivity of the compound (17.86 1 $mmol^{-1}s^{-1}$), markedly shortened T1 tissue relaxation times were able to be measured (factor 2–3). In the prostate cancer (MATLu), the tissue concentration and the effect on the tissue relaxation times were accordingly greater than in the colon cancers (HT29 and WiDr). The shortening of the relaxation times in all the studied tumors should be sufficient for an enhancement in the NMR imaging experiment (T1-weighted spin echo sequence).

TABLE 11

Tissue relaxation time $T_1$

| $T_1$ (ms) | HT29 | WiDr | MATLu | Control |
| --- | --- | --- | --- | --- |
| liver | 174 ± 8 | 180 ± 30 | 191 ± 10 | 380 ± 30 |
| kidneys | 150 ± 12 | 159 ± 30 | 171 ± 20 | 500 ± 20 |
| muscle | 489 ± 57 | 508 ± 40 | 506 ± 10 | 580 ± 10 |
| HT29 tumor | 375 ± 32 |  |  | 840 ± 50 |
| WiDr tumor |  | 358 ± 70 |  | 760 ± 100 |
| MATLu |  |  | 361 ± 65 | 1024 ± 22 |

TABLE 12

Tissue relaxation time $T_2$

| $T_2$ (ms) | HT29 | WiDr | MATLu | Control |
|---|---|---|---|---|
| liver | 49 ± 2 | 53 ± 5 | 51 ± 2 | 51 ± 2 |
| kidneys | 59 ± 3 | 64 ± 2 | 60 ± 1 | 69 ± 4 |
| muscle | 56 ± 2 | 62 ± 3 | 54 ± 2 | 58 ± 5 |
| HT29 tumor | 94 ± 7 | | | 101 ± 8 |
| WiDr tumor | | 110 ± 9 | | 118 ± 19 |
| MATLu | | | 102 ± 10 | 142 ± 14 |

EXAMPLE 24

On a Bruker Biospec nuclear spin tomograph (2.35 Tesla), the signal intensity change in various tissues of tumor-bearing (HT29 and WiDr colon cancer) nude mice (Balb/c nu/nu) was studied after i.v. administration of 0.05 mmol/kg of the compound according to example 2c (10 mmol/l, pH 7.2; 37° C. in bidistilled water). The measurement takes place with a multi slice single echo sequence (MSSE). Imaging parameters: TR: 400 ms, TE: 30 ms, layer thickness: 4 mm, number of averages: 4/slice, matrix $256^2$. After a preliminary image, 0.05 mmol/kg of the substance was administered and the signal intensity change (relative to an internal standard) was studied 5, 30, 60, 120 and 180 minutes

TABLE 13

Enhancement after intravenous administration of 0.05 mmol/kg of body weight

| Time (minutes) | liver | muscle | HT29 | WiDr | Kidneys |
|---|---|---|---|---|---|
| 0 | 100 | 100 | 100 | 100 | 100 |
| 5 | 173 ± 31 | 143 ± 23 | 171 ± 14 | 165 ± 39 | 169 ± 45 |
| 30 | 157 ± 30 | 157 ± 29 | 169 ± 14 | 170 ± 32 | 211 ± 33 |
| 60 | 170 ± 16 | 120 ± 8 | 168 ± 12 | 153 ± 33 | 207 ± 31 |
| 120 | 179 ± 37 | 126 ± 10 | 178 ± 32 | 153 ± 0 | 191 ± 37 |
| 180 | 167 ± 7 | 112 ± 9 | 136 ± 23 | 117 ± 33 | 136 ± 25 |

As early as 5 minutes p.i., a marked signal intensity increase in the liver tissue and in both studied tumors occurred. However, only a small change was noted in the muscle as reference tissue. This effect lasted during the entire observation time. The greatest signal intensity difference can be noted at 2 hours p.i. or 3 hours p.i. Only in the kidneys can an even stronger signal intensity change be noted, up to 2 hours p.i.

EXAMPLE 25

9 nude mice (Balb/c nu/nu) with subcutaneously implanted colon cancers (HT29, WiDr) were each administered by i.v. 0.1 mmol/kg of the mesoporphyrin derivative of example 8e (10 mmol/l dissolved in bidistilled water, pH 7.2, 37° C.). After 0.5, 3 and 24 hours, the animals were killed and dissected. The tissue concentrations were determined after corresponding working-up ($HNO_3$ conc.) by ICP-AES and calculated for % of the administered dose per gram of tissue net weight.

TABLE 14

% of the administered dose per gram of tissue net weight

| | over 0.5 hour MW ± S | over 3 hours MW ± S | over 24 hours MW ± S |
|---|---|---|---|
| blood | 23.59 ± 1.54 | 13.84 ± 1.34 | 2.82 |
| liver | 8.94 ± 0.24 | 15.12 ± 0.23 | 29.73 |
| kidneys | 18.90 ± 1.65 | 22.68 ± 1.39 | 22.69 |
| spleen | 6.67 ± 0.60 | 7.45 ± 0.72 | 11.34 |
| muscle | 2.39 ± 0.18 | 1.64 ± 0.01 | 1.13 |
| intestine | 3.08 ± 0.36 | 3.23 ± 0.26 | 4.63 |
| skin | 5.17 ± 0.68 | 6.67 ± 1.04 | 5.26 |
| lung | 13.99 ± 0.61 | 8.46 ± 1.35 | 4.69 |
| HT29 tumor | 2.57 ± 0.31 | 3.31 ± 0.27 | 2.84 |
| WiDr tumor | 2.90 ± 0.21 | 4.12 ± 0.32 | 3.93 |
| rest of body | 3.65 ± 0.18 | 3.88 ± 0.97 | 2.48 |

While in the liver tissue, the increase is from 10% of the administered dose per gram of tissue net weight (0.5 hour p.i.) to about 30% of the dose per gram of tissue net weight within 24 hours p.i., the tissue concentrations in all other tissues decrease within 24 hours or at least remain constant. Thus the liver has the absolutely highest tissue concentration of all studied tissues 24 hours p.i.

EXAMPLE 26

9 nude mice (Balb/c nu/nu) with subcutaneously implanted colon cancers (HT29, WiDr) were each administered by i.v. 0.1. mmol/kg of the mesoporphyrin derivative of example 16f (10 mmol/l dissolved in bidistilled water, pH 7.2, 37° C.). After 0.5 and 3 hours the animals were killed and dissected. The tissue concentrations were determined after corresponding working-up ($HNO_3$ conc.) by ICP-AES and calculated for % of the administered dose per gram of tissue net weight.

TABLE 15

% of the administered dose per gram of tissue net weight (% of d. dose/g of organ)

| | for 0.5 hour MW ± S | for 3 hours MW ± S |
|---|---|---|
| blood | 30.68 ± 0.85 | 11.63 ± 4.46 |
| liver | 20.91 ± 9.96 | 27.93 ± 2.57 |
| kidneys | 8.40 ± 1.58 | 9.72 ± 1.80 |
| spleen | 11.31 ± 1.51 | 15.50 ± 2.96 |
| muscle | 3.53 ± 0.88 | 3.31 ± 2.90 |
| intestine | 2.06 ± 0.67 | 2.75 ± 0.30 |
| skin | 4.17 ± 1.35 | 7.12 ± 1.45 |
| lung | 21.54 ± 0.94 | 15.28 ± 2.68 |
| HT29 tumor | 4.47 ± 2.06 | 3.16 ± 0.95 |
| WiDr tumor | 3.24 ± 1.23 | 6.30 ± 2.22 |
| rest of body | 3.69 ± 0.95 | 3.91 ± 0.43 |

The liver showed the strongest concentration of all the studied tissues with about 21 and 28%, respectively, of the administered dose per gram of tissue net weight at 0.5 and 3 hours p.i., respectively.

EXAMPLE 27

9 nude mice (Balb/c nu/nu) with subcutaneously implanted colon cancers (HT29, WiDr) were each administered by i.v. 0.1 mmol/kg of the mesoporphyrin derivative of example 18d (10 mmol/l dissolved in bidistilled water, pH 7.2, 37° C.). After 0.5 and 3 hours, the animals were killed and dissected. The tissue concentrations were determined after corresponding working-up (HNO$_3$ conc.) by ICP-AES and calculated for % of the administered dose per gram of tissue net weight.

TABLE 16

| % of the administered dose per gram of tissue net weight | | |
|---|---|---|
| | for 0.5 hour MW ± S | for 3 hours MW ± S |
| blood | 24.44 ± 2.32 | 16.95 ± 1.53 |
| liver | 13.28 ± 2.90 | 16.89 ± 1.15 |
| kidneys | 11.74 ± 2.38 | 20.41 ± 1.88 |
| spleen | 7.52 ± 0.40 | 10.82 ± 0.87 |
| muscle | 0.89 ± 0.17 | 1.04 ± 0.06 |
| intestine | 4.93 ± 0.90 | 2.31 ± 0.28 |
| skin | 3.71 ± 0.52 | 4.46 ± 0.53 |
| lung | 17.70 ± 2.50 | 17.56 ± 3.34 |
| HT29 tumor | 1.48 ± 0.28 | 3.53 ± 0.52 |
| WiDr tumor | 1.94 ± 0.78 | 4.50 ± 0.98 |
| rest of body | 2.38 ± 0.27 | 2.43 ± 0.13 |

The studied substance shows a concentration in the liver tissue with about 14 and 17%, respectively, of the administered dose per gram of tissue net weight 0.5 and 2 hours p.i., respectively. In other studied tissues, with the exception of the kidneys, the tissue concentrations in some cases are considerably lower (factor 5 to 10).

EXAMPLE 28

9 nude mice (Balb/c nu/nu) with subcutaneously implanted colon cancers (HT29, WiDr) were each administered by i.v. 0.1 mmol/kg of the mesoporphyrin derivative of example 19e (10 mmol/l dissolved in bidistilled water, pH 7.2, 37° C.). After 0.5, 3 and 24 hours, the animals were killed and dissected. The tissue concentrations were determined after corresponding working-up (HNO$_3$ conc.) by ICP-AES and calculated for % of the administered dose per gram of tissue net weight.

TABLE 17

| % of the administered dose per gram of tissue net weight | | | |
|---|---|---|---|
| | over 0.5 hour MW ± S | over 3 hours MW ± S | over 24 hours MW ± S |
| blood | 11.68 ± 2.18 | 4.13 ± 3.62 | 0.06 ± 0.01 |
| liver | 15.07 ± 1.35 | 13.75 ± 1.54 | 10.43 ± 1.56 |
| kidneys | 26.52 ± 9.65 | 9.98 ± 0.50 | 7.87 ± 0.54 |
| spleen | 7.38 ± 2.40 | 4.41 ± 1.41 | 4.00 ± 1.71 |
| muscle | 1.79 ± 0.34 | 0.35 ± 0.09 | 0.17 ± 0.07 |
| intestine | 2.56 ± 0.50 | 5.43 + 1.08 | 0.61 + 0.43 |
| skin | 7.13 ± 1.95 | 2.68 ± 0.39 | 1.26 ± 0.12 |
| lung | 10.14 ± 1.53 | 2.51 ± 0.36 | 0.69 ± 0.13 |
| HT29 tumor | 3.86 ± 1.06 | 2.22 ± 0.31 | 0.99 ± 0.33 |
| WiDr tumor | 6.15 ± 2.27 | 5.45 ± 6.63 | 1.95 ± 0.54 |
| rest of body | 3.37 ± 0.51 | 1.18 ± 3.06 | 0.62 ± 0.27 |

Except for the liver, the tissue concentration decreases quickly within 24 hours (factor 5–20 relative to 0.5 hour p.i.). The liver had the absolutely highest tissue concentrations of all the studied tissues with about 14 and 10%, respectively, of the administered dose per gram of tissue net weight 3 and 24 hours p.i., respectively.

EXAMPLE 29

On a Siemens Magneton$^{(R)}$ (1.5 Tesla; 64 MHz), the signal intensity in various tissues of a tumor-bearing rabbit [hare rabbit, Wulf, female, approximately 4 kg body weight (n=3), tumor of VX-2 carcinoma implanted intramuscularly about 3 weeks before the beginning of the test) was studied after the i.v. administration of 0.0025 mmol/kg body weight (corresponding to 0.05 mmol/kg of gadolinium) of the compound according to the invention produced according to Example 1c. The measurement took place with the following imaging parameters: T$_1$-weighted spin echo sequence: T$_R$: 350 ms, T$_E$: 15 ms, layer orientation: coronary, layer thickness 3 mm, number of averages: 4 per layer, field of view: 150 mm, matrix 256$^2$, 4–6 layers 1 echo per imaging sequence.

The administration resulted in a good long acting enhancement, namely both in the implanted tumor and in the majority of the lymph nodes on the tumor-bearing side. Because of the pronounced enhancement in these lymph nodes or lymph node areas, after administration of the compound according to the invention, a metastasis attack of the lymph nodes could therefore be diagnosed. The histological study of the lymph nodes confirmed the results of the MR-tomographic study.

Figure 4:
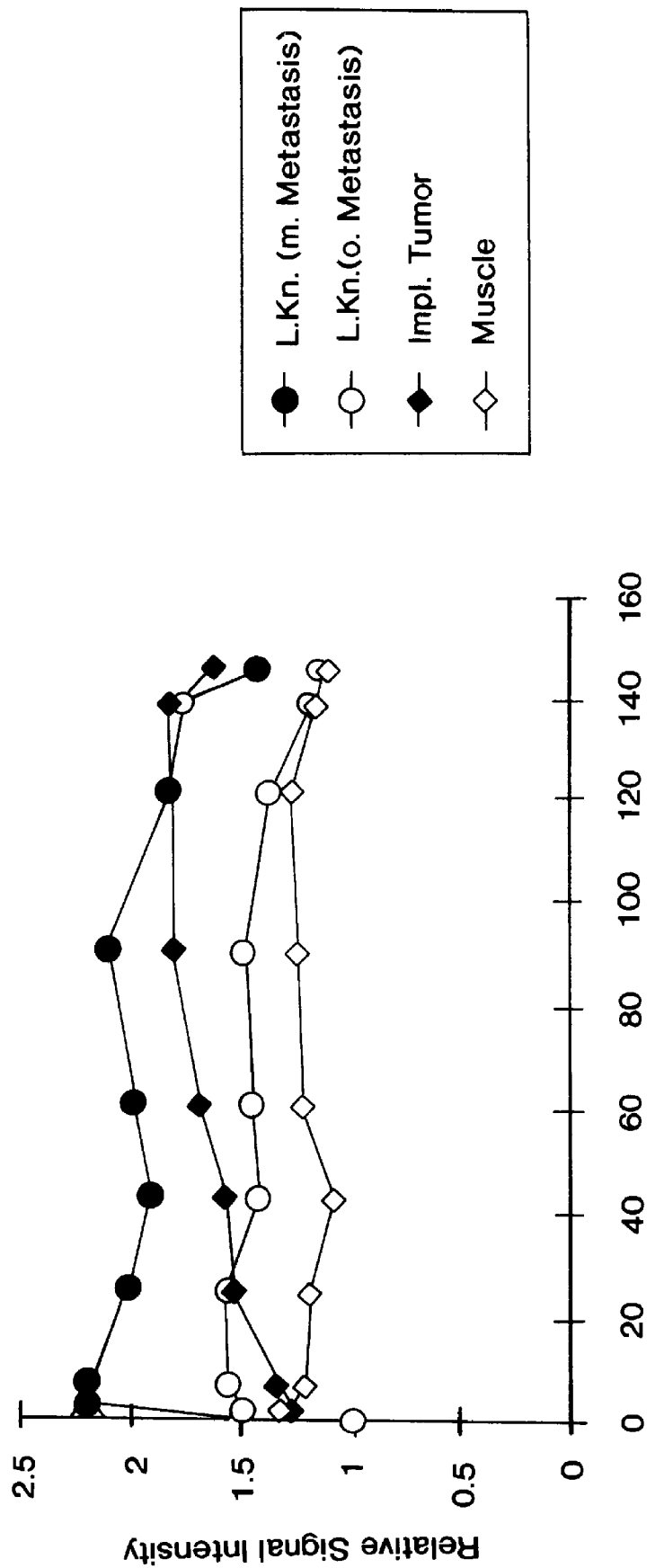

The relative signal intensities in various tissues are represented in FIG. 4. The output signal intensity (=SI$_{precontrast}$) in the various tissues was set equal to 1 in each case.

We claim:

1. A porphyrin complex compound of a ligand of formula I

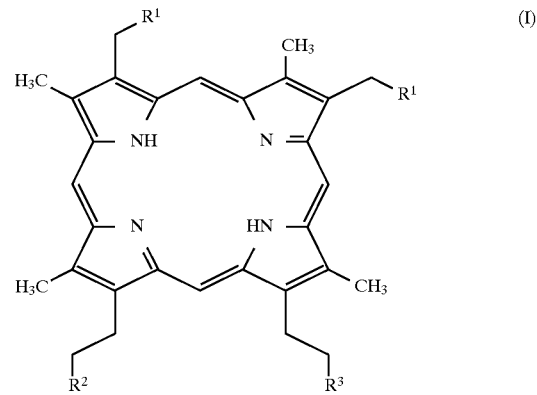

and at least one ion of an element with atomic numbers 21–32, 37–39, 42–51 or 57–83, in which R$^1$ is a hydrogen atom, a straight-chain C$_1$–C$_6$ alkyl radical, a C$_7$–C$_{12}$ aralkyl radical or a group OR' in which R' is a C$_1$–C$_3$ alkyl radical, R$^2$ is a group =CO—Z or a group —(NH)$_o$—(A)$_q$—NH—D, in which Z is a group —OL, with L meaning an inorganic or organic cation or Z is a (C$_1$–C$_4$ alkyl radical, A is a phenylenoxy or a C$_1$–C$_{12}$ alkylene or C$_7$–C$_{12}$-aralkylene group interrupted by one or more oxygen atoms, o an q, independently of one another, are the numbers 0 or 1 and D is a hydrogen atom or a group —CO—A—(COOL)$_o$—(H)$_m$, with m equal to 0 or 1 and the sum of m and o equal to 1, or R$^2$ has one of the definitions for R$^3$, R$^3$ is a group —(C=M)(NR$^4$)$_o$—(A)$_q$—(NR$^5$)—K, in which M is an oxygen atom or two hydrogen atoms, R$^4$ is a group —(A)$_q$—H and K is a complexing agent of formula (IIa) or (IIb) and in which R$^5$, if K is a complexing agent of formula (IIa), has the same meaning as R$^4$, and R$^5$, if K is a complexing agent of formula (IIb), has the same meaning as D, provided that a direct oxygen-nitrogen bond is not allowed, and K is a complexing agent of general formula (IIa) or (IIb)

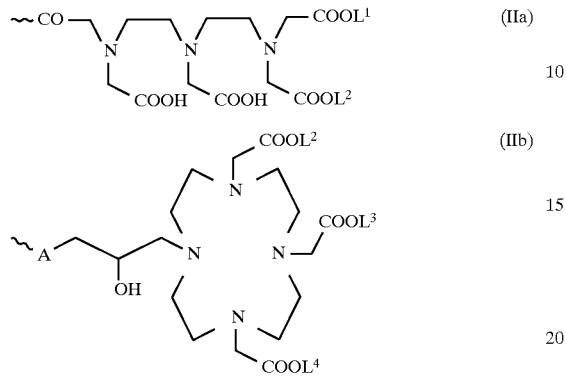

wherein $L^1$ is a $C_1$–$C_6$ alkyl radical or an inorganic or organic cation and $L^2$, $L^3$ and $L^4$, independently of one another, have the meaning of $L^1$ or a hydrogen atom, provided that at least two free carboxylic acid groups are present in the complexing agent, and optionally other anions to compensate for optionally present charges in the metalloporphyrin.

2. A complex compound according to claim 1, wherein the porphyrin system contains a metal ion.

3. A complex compound according to claim 1, wherein the porphyrin system contains no metal ion.

4. A compound according to claim 1, which is the disodium salt of the digadolinium complex of manganese(III)-{N,N'-bis-3,8-bis(1-propyl)-deuteroporphyrin-IX-13,17-diamide}-acetate.

5. A compound according to claim 1, which is the digadolinium complex of the manganese(III)-{N,N'-bis-3,8bis(1-propyl)-deuteroporphyrin-IX-13,17-diamide}-acetate.

6. A pharmaceutical composition comprising at least one complex compound according to claim 1 and a pharmaceutically acceptable carrier.

7. A process for the production of a porphyrin complex which is a ligand of general formula I

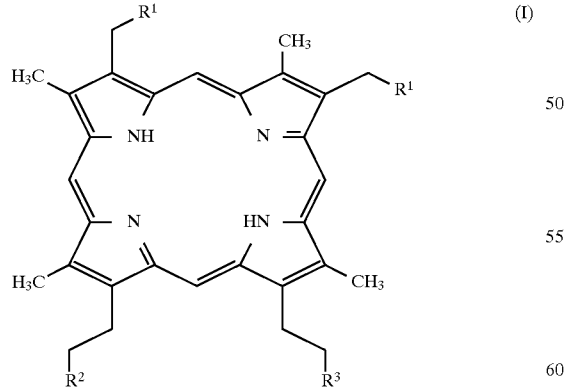

and at least one ion of an element with atomic numbers 21–32, 37–39, 42–51 or 57–83, in which $R^1$ is a hydrogen atom, a straight-chain $C_1$–$C_6$ alkyl radical, a $C_7$–$C_{12}$ aralkyl radical or a group OR' in which R' is a $C_1$–$C_3$ alkyl radical, $R^2$ is a group =CO—Z or a group —(NH)$_o$—(A)$_q$—NH—D, in which Z is a group —OL, with L meaning an inorganic or organic cation or Z is a $C_1$–$C_4$ alkyl radical, A is a phenylenoxy or a $C_1$–$C_{12}$ alkylene or $C_7$–$C_{12}$-aralkylene group interrupted by one or more oxygen atoms, o an q, independently of one another, are the numbers 0 or 1 and D is a hydrogen atom or a group —CO—A—(COOL)$_o$—(H)$_m$, with m equal to 0 or 1 and the sum of m and o equal to 1, or $R^2$ has one of the definitions for $R^3$, $R^3$ is a group —(C=M)(NR$^4$)$_o$—(A)$_q$—(NR$^5$)—K, in which M is an oxygen atom or two hydrogen atoms, $R^4$ is a group —(A)$_q$—H and K is a complexing agent of formula (IIa) or (IIb) and in which $R^5$, if K is a complexing agent of formula (IIa), has the same meaning as $R^4$, and $R^5$, if K is a complexing agent of formula (IIb), has the same meaning as D, provided that a direct oxygen-nitrogen bond is not allowed, and K is a complexing agent of general formula (IIa) or (IIb)

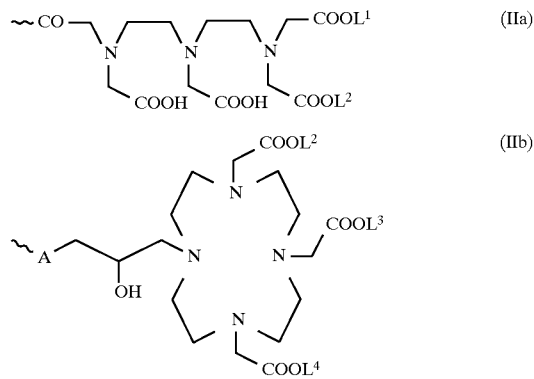

wherein $L^1$ is a $C_1$–$C_6$ alkyl radical or an inorganic or organic cation and $L^2$, $L^3$ and $L^4$, independently of one another, have the meaning of $L^1$ or a hydrogen atom, provided that at least two free carboxylic acid groups are present in the complexing agent, and optionally other anions to compensate for optionally present charges in the metalloporphyrin, comprising:

a) reducing a porphyrin of general formula (IIIa)

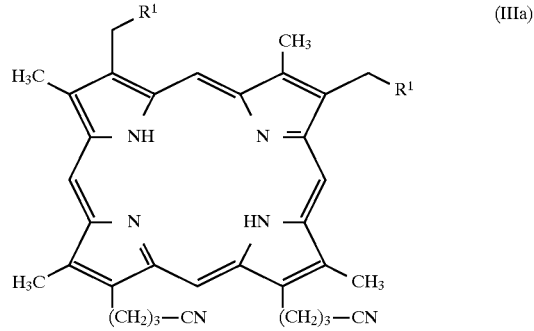

b) reacting a porphyrin of general formula (IIIb)

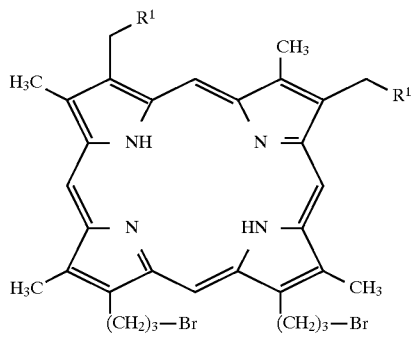
(IIIb)

with aminophenol, or
c) reacting a porphyrin of general formula (IIIc)

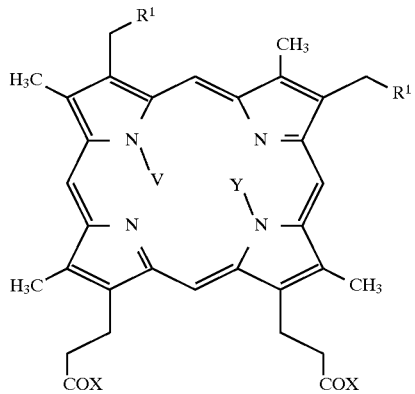
(IIIc)

in which $R^1$ has the indicated meaning,
V and Y each stand for a hydrogen atom or together for a multivalent metal ion of an element with atomic numbers 21–32, 37–39, 42–51 or 57–83, and
X stands for a halogen atom, a group —OR', or for a group —O— with a compound of the formula $H-NR^4-(A)_q-NR^4-H$,
in which A, $R^4$ and q have the indicated meaning, optionally subsequently reducing the carbonyl groups or performing Hofmann degradation of the amide
to yield a porphyrin of general formula IV

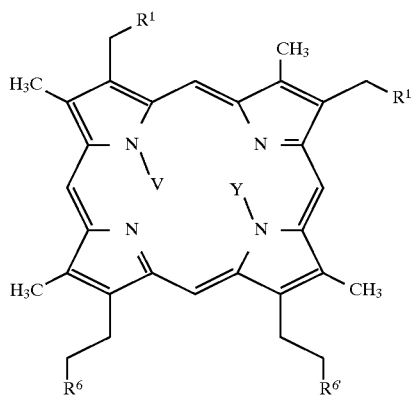
(IV)

in which $R^6$ stands for a group $-(C=M)-(NR^4)_o-(A)_q-NR^4-H$,
in which M, $R^4$, A, o and q have the indicated meaning and in which $R^{6'}$ has the same meaning as $R^6$ or stands for a group —OR', then reacting IV with a complexing agent of general formula V,

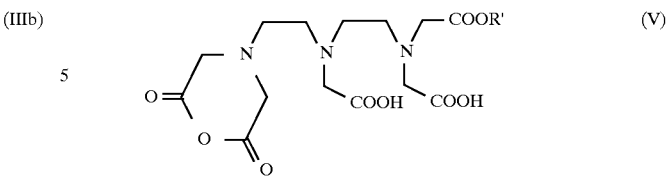
(V)

in which R' has the indicated meaning, and optionally ester groups present are saponified or
reacting IV with a compound of formula VI

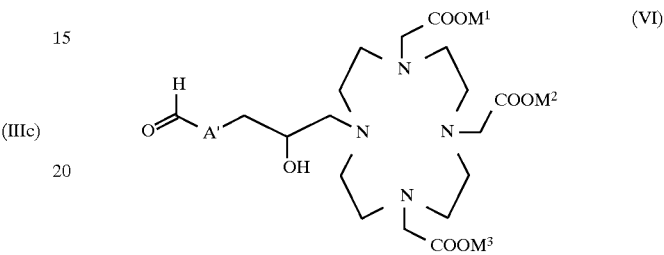
(VI)

in which A' is a group A shortened by one carbon atom and $M^1$, $M^2$ and $M^3$, independently of one another, stand for $R^1$ or a metal ion equivalent of the elements with atomic numbers 21–32, 37–39, 42–51 or 57–83, under reductive amination conditions, thereafter the thus obtained product—optionally after complete or partial cleavage of the ester groups—is reacted with at least one metal oxide or metal salt of the elements with the above-mentioned atomic numbers, and acylated with a nucleofuge-D' reagent or first acylated and then reacted with said metal oxide or metal salt, in which D' has the meaning indicated under D, with the provision that D' does not stand for hydrogen and finally, optionally, acidic hydrogens optionally present are then completely or partially substituted by cations of inorganic or organic bases.

8. A process for the production of a pharmaceutical composition according to claim 6, comprising bringing the complex compound dissolved or suspended in water or physiological salt solution, optionally with the additives usual in galenicals, into a form suitable for enteral or parenteral administration.

9. A pharmaceutical compound according to claim 6, further comprising a conventional galenical additive.

10. A method for taking a radiodiagnostic or NMR measurement, comprising subjecting a subject to such measurement in conjunction with administering a complex compound according to claim 1.

11. A method according to claim 10, wherein the radiodiagnostic measurement is nuclear spin tomography or position emission tomography.

12. A method for radiotherapy, comprising administering a complex compound according to claim 1.

13. A complex compound according to claim 1, wherein $R^1$ is a hydrogen atom, a straight-chain $C_{1-6}$-alkyl radical or a $C_{7-12}$-aralkyl radical.

14. A compound according to claim 1, which is the disodium salt of the digadolinium complex of N,N'-bis[9-carboxylato-2,5,8-tris(carboxylatomethyl)-2,5,8-triazanonyl-carbamoyl]-mesoporphyrin-IX-13,17-diamide.

* * * * *

UNITED STATES PATENT AND TRADEMARK OFFICE
CERTIFICATE OF CORRECTION

PATENT NO. : 5,849,259
DATED : December 15, 1998
INVENTOR(S) : Hilger et al.

Page 1 of 1

It is certified that error appears in the above-identified patent and that said Letters Patent is hereby corrected as shown below:

IN THE CLAIMS:

Claim 1,
Line 10: Delete " =C-Z " and insert -- -C-Z -- therefor.
Line 17: Delete "o an q" and insert -- o and q -- therefor.

Claim 7,
Line 10: " =C-Z " and insert -- -C-Z -- therefor.
Liner 17: Delete "o an q" and insert -- o and q -- therefor.

Signed and Sealed this

Seventh Day of August, 2001

*Attest:*

NICHOLAS P. GODICI
*Attesting Officer*     *Acting Director of the United States Patent and Trademark Office*